(12) United States Patent
Janssen et al.

(10) Patent No.: US 8,247,524 B2
(45) Date of Patent: *Aug. 21, 2012

(54) PREPARATION OF SUPRAMOLECULAR POLYMERS CONTAINING QUADRUPLE HYDROGEN BONDING UNITS IN THE POLYMER BACKBONE

(75) Inventors: Hendricus Marie Janssen, Eindhoven (NL); Gaby Maria Leonarda Van Gemert, Helmond (NL); Egbert Willem Meijer, Waalre (NL); Anton Willem Bosman, Eindhoven (NL)

(73) Assignee: Suprapolix B.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/907,737

(22) Filed: Oct. 19, 2010

(65) Prior Publication Data
US 2011/0034641 A1    Feb. 10, 2011

Related U.S. Application Data

(63) Continuation of application No. 10/577,946, filed as application No. PCT/NL03/00766 on Nov. 4, 2003, now Pat. No. 7,838,621.

(51) Int. Cl.
*C08G 69/00*    (2006.01)
*C08G 18/00*    (2006.01)
*C08G 18/32*    (2006.01)
*C08G 18/42*    (2006.01)
*C08G 18/48*    (2006.01)
*C08G 18/71*    (2006.01)

(52) U.S. Cl. .................. 528/327; 528/480
(58) Field of Classification Search .......... 528/327, 528/480
See application file for complete search history.

(56) References Cited

U.S. PATENT DOCUMENTS

| | | |
|---|---|---|
| 3,388,087 A | 6/1968 | Dieterich et al. |
| 3,480,592 A | 11/1969 | Dieterich et al. |
| 4,093,759 A | 6/1978 | Otsuki et al. |
| 4,136,092 A | 1/1979 | Jackle et al. |
| 4,140,759 A | 2/1979 | Mausner |
| 4,216,318 A | 8/1980 | Brown et al. |
| 4,322,327 A | 3/1982 | Yoshimura et al. |
| 4,684,728 A | 8/1987 | Mohring et al. |
| 4,942,035 A | 7/1990 | Churchill et al. |
| 5,410,016 A | 4/1995 | Hubbell et al. |
| 5,500,209 A | 3/1996 | Ross et al. |
| 5,548,035 A | 8/1996 | Kim et al. |
| 5,610,268 A | 3/1997 | Meijer et al. |
| 5,631,337 A | 5/1997 | Sassi et al. |
| 5,723,563 A | 3/1998 | Lawrey et al. |
| 5,736,535 A | 4/1998 | Bernstein et al. |
| 5,874,069 A | 2/1999 | Mendolia et al. |
| 5,883,211 A | 3/1999 | Sassi et al. |
| 5,919,441 A | 7/1999 | Mendolia et al. |
| 6,320,018 B1 | 11/2001 | Sijbesma et al. |
| 6,353,076 B1 | 3/2002 | Barr et al. |
| 6,489,397 B2 | 12/2002 | Kim et al. |
| 6,534,072 B2 | 3/2003 | Mondet et al. |
| 6,683,151 B1 | 1/2004 | Loontjens et al. |
| 6,716,370 B2 | 4/2004 | Kendig |
| 6,743,767 B2 | 6/2004 | Goldoni et al. |
| 6,803,447 B2 | 10/2004 | Janssen et al. |
| 6,803,477 B2 | 10/2004 | Prakash et al. |
| 6,818,018 B1 | 11/2004 | Sawhney |
| 6,899,992 B2 | 5/2005 | Huang et al. |
| 6,911,296 B2 | 6/2005 | Pappas et al. |
| 6,939,938 B2 | 9/2005 | Benard et al. |
| 6,972,304 B2 | 12/2005 | Smith et al. |
| 7,196,073 B2 | 3/2007 | Marciani |
| 7,622,131 B2 | 11/2009 | Bosman et al. |
| 7,736,663 B2 | 6/2010 | Cooper et al. |
| 7,838,621 B2 | 11/2010 | Janssen et al. |
| 7,862,805 B2 | 1/2011 | Mougin et al. |
| 2003/0015185 A1 | 1/2003 | Dutart |
| 2003/0092838 A1 | 5/2003 | Fomperie et al. |
| 2003/0158403 A1 | 8/2003 | Manoharan et al. |
| 2004/0023155 A1 | 2/2004 | Hayakawa et al. |
| 2004/0087755 A1 | 5/2004 | Eling et al. |
| 2007/0149751 A1 | 6/2007 | Lindsay et al. |
| 2007/0264208 A1 | 11/2007 | Mougin et al. |
| 2008/0260795 A1 | 10/2008 | Baughman et al. |
| 2009/0004274 A1 | 1/2009 | Hoorne-Van Gemert et al. |

(Continued)

FOREIGN PATENT DOCUMENTS
EP    0 259 92    9/1983
(Continued)

OTHER PUBLICATIONS

Coates, G.W., et al., "Polymerization of Ureidopyrimidinone-Functionalized Olefings by Using Late-Transition Metal Ziegler-Natta Catalysts: Synthesis of Thermoplastic Elastomeric Polyolefins," Angew. Chem. Int. Ed. 2001, vol. 40, No. 11, 2153.

(Continued)

*Primary Examiner* — Duc Truong
(74) *Attorney, Agent, or Firm* — Gilberto M. Villacorta; Sunit Talapatra; Foley & Lardner LLP

(57) ABSTRACT

The present invention relates to a supramolecular polymer comprising quadruple hydrogen bonding units within the polymer backbone, wherein at least a monomer comprising a 4H-unit is incorporated in the polymer backbone via at least two reactive groups up to four reactive groups, provided that the 4H-units are not covalently incorporated in the polymer backbone through one or more silicon-carbon bonds. The invention also relates to processes for preparing such supramolecular polymers and their use in personal care applications, surface coatings, imaging technologies, biomedical applications, (themo)reversible coatings, adhesive and sealing compositions and as thickening agents, gelling agents and binders.

17 Claims, No Drawings

U.S. PATENT DOCUMENTS

| | | | |
|---|---|---|---|
| 2009/0111930 | A1 | 4/2009 | Van Gemert et al. |
| 2009/0130172 | A1 | 5/2009 | Dankers et al. |
| 2010/0076147 | A1 | 3/2010 | Hoorne-Van Gemert et al. |
| 2011/0229724 | A1 | 9/2011 | Hoorne-Van Gemert et al. |

FOREIGN PATENT DOCUMENTS

| | | |
|---|---|---|
| EP | 0 433 188 A1 | 6/1991 |
| EP | 0 744 428 A2 | 11/1996 |
| EP | 0 683 769 B1 | 7/1998 |
| EP | 1 213 309 A1 | 6/2002 |
| EP | 1310533 | 5/2003 |
| EP | 0 877 055 A | 9/2004 |
| EP | 1 392 222 | 9/2007 |
| FR | 2657082 A1 | 7/1991 |
| FR | 2825628 | 12/2002 |
| JP | 52-074692 A | 6/1977 |
| JP | 2004-250623 A | 9/2004 |
| WO | WO 98/14504 | 4/1998 |
| WO | WO-98/14505 A1 | 4/1998 |
| WO | WO-99/07343 A1 | 2/1999 |
| WO | WO-01/44307 A2 | 6/2001 |
| WO | WO 02/46260 | 6/2002 |
| WO | WO 02/098377 | 12/2002 |
| WO | WO-03/032929 A2 | 4/2003 |
| WO | WO 03/059964 | 7/2003 |
| WO | WO-03/099875 A2 | 12/2003 |
| WO | WO 2004/015698 | 2/2004 |
| WO | WO 2004/052963 | 6/2004 |
| WO | WO-2005/042641 A1 | 5/2005 |
| WO | WO-2006/006855 A1 | 1/2006 |
| WO | WO-2006/118460 A1 | 11/2006 |
| WO | WO-2006/118461 A2 | 11/2006 |
| WO | WO-2007/058539 A2 | 5/2007 |
| WO | WO-2007/072000 A1 | 6/2007 |
| WO | WO-2008/063057 A3 | 5/2008 |
| WO | WO-2010/002262 A1 | 1/2010 |

OTHER PUBLICATIONS

Flory, P.J., "Random Reorganization of Molecular Weight Distribution in Linear Condensation Polymers," J. Am. Chem. Soc. 1942, vol. 64, p. 2205.

Folmer, B.J.B., et al., "Supramolecular Polymer Materials: Chain Extension of Telechelic Polymers Using a Reactive Hydrogen-Bonding Synthon," Adv. Mater. 2000, vol. 12, 874.

Hirschberg, et al., "Supramolecular Polymers from Linear Telechelic Siloxanes with Quadruple-Hydrogen-Bonded Units," Macromolecules 1999, 32, 2696-2705.

Korshak, V.V., and Vasnev, V.A.; Comprehensive Polymer Science; Pergamon Press; London, 1989; vol. 5, p. 131.

Lange, R.F.M., et al., "Hydrogen-Bonded Supramolecular Polymer Networks," Journal of Polymer Science: Part A: Polymer Chemistry, vol. 37, 3657-3670 (1999).

Lange, R.F.M., et al., "Supramolecular Polymer Interactions Based on the Alternating Copolymer of Styrene and Maleimide," Macromolecules 1995, vol. 28, 782.

Brunsveld L et al., "Supramolecular Polymers", Chemical Reviews, vol. 1, Dec. 2001, pp. 4071-4097, XP002267453.

Kato T., "Supramolecular liquid crystal polymers. Formation of Molecular Self-Organized Structures and Their Functionalization", Kobunshi Ronbunshu (Japanese Polymer Science and Technology.

El-Ghayoury A et al., "Supramolecular Hydrogen-bonded oligo(p-phenylene vinylene) Polymers", Angewandte Chemi, Wiley-Vch, Weinheim, DE, vol. 40, No. 19, 2001, pp. 3660-3663. XP002260390.

Guan et al., "Modular Domain Structure: A Biomimetic Strategy for Advanced Polymeric Materials", J. Am. Chem. Soc., vol. 126, pp. 2058-2065, 2004.

Roland et al., "Synthesis of Titin-Mimicking Polymers Having Modular Structures by Using Noncovalent Interactions", Polymer Preprints, vol. 44 (1), pp. 726-727, 2003.

Guan et al., "Synthesis and Single-molecule studies of Modular Polymers Using Precise Hydrogen Bonding Interactions", Polymer Preprints, vol. 44(2), pp. 485-486, 2003.

Chemical Abstract, vol. 85, Abst. No. 15348y, Jul. 1976, 1 page.

Chemical Abstracts, vol. 80, No. 20, May 20, 1974, English abstract of JP 04 829398, filed Aug. 28, 1968, 1 page.

Chemical Abstracts, vol. 97, No. 10, Sep. 1982, Veselovskii et al., "Adhesive Composition," Inst. of the Chemistry of High Molecular Weight Compounds, Mar. 5, 1979, 1 page.

CRC Handbook of Chemistry & Physics, 59th Ed., p. E-61, 1978-1979, CRC Press, Inc, 3 pages.

Derwent 91-179975125, 1 Page.

Derwent Abstract Acc. No. 1977-55084Y, Week 197731, English abstract for JP 52-74692, Jun. 22, 1977, 3 pages.

Dieterich et al, "Polyurethane Ionomers, a New Class of Block Polymers," Angew. Chem. Int'l. Edit., vol. 9, No. 1, 1970, p. 40-50 (English version of German article in Angew. Chem., vol. 2, 1970, pp. 40-50.

Hirschberg et al., "Ureidotriazine-Based Supramolecular Copoloymers" Marcomolecules, vol. 36, 2003, pp. 1429-1432.

Hofmeier et al., "New Supramolecular Polymers Containing Both Terpyridine Metal Complexes and Quadruple Hydrogen Bonding Units," Chem. Commun., 2004, pp. 318-319.

Kautz et al., "Cooperative End-to-End and Lateral Hydrogen-Bonding Motifs in Supramolecular Thermoplastic Elastomers," Macromolecules, vol. 39, 2006, pp. 4265-4267.

Lee et al., "Hydrogels for Tissue Engineering" Chem. Rev., vol. 101, No. 7, 2001, pp. 1869-1879.

Saunders et al. (editors), "Polyurethanes—Chemistry and Technology High Polymers: Part 1. Chemistry," High Polymers, vol. XVI-Part 1, 1962, Interscience Publishers a Division of Wiley & Sons, pp. 68-73.

Sijbesma et al., "Reversible Polymers Formed from Self-Complementary Monomers Using Quadruple Hydrogen Bonding," Science, vol. 278, 1997, pp. 1601-1604.

Urbanski et al. "Potential Antimalarial Compounds. IX. Pyrimidine Derivatives of Urea and Guanidine", Journal of Medicinal Chemistry, vol. 10, 1967, pp. 521-525.

Yamauchi et al., "Thermoreversible Poly(alkyl acrylates) Consisting of Self-Complementary Multiple Hydrogen Bonding," Macromolecules, vol. 36, 2003, pp. 1083-1088.

Yamauchi et al., Abstract of "Synthesis and Characterization of Novel Multiple-Hydrogen Bonded Macromolecules Via A Michael Reaction," Dept. of Chemistry, Virginia Polytechnic Institute and State University, 1 page.

Yamauchi, et al., "Thermoreversible Polyesters Consisting of Multiple Hydrogen Bonding (MHB)," Macromolecules, vol. 37, No. 10, 2004, pp. 3519-3522.

PREPARATION OF SUPRAMOLECULAR POLYMERS CONTAINING QUADRUPLE HYDROGEN BONDING UNITS IN THE POLYMER BACKBONE

CROSS-REFERENCE TO RELATED APPLICATION

This application is a continuation of U.S. patent application Ser. No. 10/577,946, filed Aug. 25, 2006 now U.S. Pat. No. 7,838,621, which is the National Phase of International Patent Application No. PCT/NL2003/000766, filed Nov. 4, 2003, and published as WO 2005/042641, on May 12, 2005. The contents of these applications are incorporated herein by reference in their entirety.

FIELD OF THE INVENTION

The invention relates to supramolecular polymers comprising quadruple hydrogen bonding units within the polymer backbone. The supramolecular polymers can be prepared by (i) chain extension or (ii) redistribution. In chain extension, a monomer containing (a precursor of) a quadruple hydrogen bonding group is copolymerized with a macromonomer of choice, whereas in redistribution a polymer of choice is reacted with a monomer containing a quadruple hydrogen bonding unit. The resulting supramolecular polymers show unique new characteristics due to the presence of additional physical interactions between the polymer chains that are based on multiple hydrogen bonding interactions (supramolecular interactions).

BACKGROUND OF THE INVENTION

This invention relates to supramolecular polymers comprising quadruple hydrogen bonding units that are capable of forming at least four H-bridges with each other leading to physical interactions between different polymer chains. The physical interactions originate from multiple hydrogen bonding interactions (supramolecular interactions) between self-complementary units comprising at least four hydrogen bonds in a row. Units capable of forming at least four hydrogen bonds, i.e. quadruple hydrogen bonding units, are in this patent application abbreviated as 4H-units, 4H-elements or structural elements (4H) and are used in this patent application as interchangeable terms. Sijbesma et al. (U.S. Pat. No. 6,320,018; Science, 278, 1601; incorporated by reference herein) discloses such self-complementary units which are based on 2-ureido-4-pyrimidones.

Telechelic polymers or trifunctional polymers have been modified with 4H-units (Folmer, B. J. B. et al., Adv. Mater. 2000, Vol. 12, 874; Hirschberg et al., Macromolecules 1999, Vol. 32, 2696; Lange, R. F. M. et al, J. Polym. Sci, Part A, 1999, 37, 3657-3670). However, these polymers have the 4H-unit coupled at the ends of the polymers, so the number of end groups is therefore limited by the amount of end groups (normally 2), and the functional units are always located on the periphery of the polymer.

Polymers containing hydrogen bonding groups grafted on the main chain that are synthesized via copolymerization of hydrogen bonding monomers have been obtained with hydrogen bonding units containing three H-bonds in a row (Lange F. M. et al., Macromolecules 1995, Vol 28, 782). However, only an alternating copolymer of styrene and maleimide can be used in this approach, and moreover, the H-bonding interactions between the polymers are much weaker than the H-bonding based on the 4H-units, obviously resulting in poorer material properties.

Polymers with quadruple H-bonding units grafted on the main chain have been obtained by copolymerizing an olefin bearing a 4H-unit with a common olefin (Coates, G. W. et al., Angew. Chem. Int. Ed., 2001, Vol. 40, 2153). However, complex chemistry has to be used to prepare and to polymerize the monomer and, due to the intrinsic sensitivity of the catalyst needed to obtain the polymer, severe limitations hinder the general use of this system and limits it to tailor-made polyolefin systems. For example, Coates et al. discloses the copolymerization of 1-hexene and a 6-hexenyl-2-ureido-4-pyrimidone derivative with a Ziegler-Natta type nickel based catalyst and diethylaluminum chloride as cocatalyst. Another drawback of the method according to Coates et al. is that the amount of 4H-units that can be incorporated in the copolymer is rather limited, i.e. typically about 2 mol %.

WO 02/46260 discloses polyurethane based polymers with H-bonding units as end-cappers and optionally grafted with H-bonding units that can be used as hot melt adhesive or TPU-foam. WO 02/098377 discloses polymers with H-bonding units as end groups that can be used in cosmetic compositions. Both patent applications use comparable or the same chemistry as described in the papers above.

U.S. Provisional Patent Application No. 60/403,636, filed Aug. 16, 2002, and PCT/NL03/00586, filed Aug. 15, 2003, incorporated by reference herein for the US patent practice, discloses simpler chemistry to acquire polymers with grafted quadruple H-bonding units. For example, polyacrylates and polymethacrylates with grafted 4H-units have been produced using different kinds of polymerization techniques.

U.S. Provisional Patent Application No. 60/431,712, filed Dec. 3, 2002, incorporated by reference herein for the US patent practice, discloses polysiloxanes comprising 4H-units in the polymer backbone. More precisely, polysiloxanes are disclosed having (a) 4H-units directly incorporated in the polymer backbone, wherein the 4H-units are incorporated via two linkers and are covalently attached through a silicon-carbon bond or (b) 4H-units pending from the polymer backbone, wherein the 4H-units are covalently attached via one linker through a silicon-carbon bond.

The present invention discloses polymers comprising 4H-units within the polymer backbone that can easily be prepared by chain extending a functional macromonomer with a functional monomer comprising a 4H-unit (or a precursor of such a unit). Alternatively, redistribution reactions of polymers with functional monomers comprising a 4H-unit can be employed. The invention allows for control over the average amount of 4H-units per polymer chain by setting the molar ratio between the reacting species.

The supramolecular according to the present invention are unprecedented, because they comprise multiple 4H-units as an integral part of the polymeric main chain. Also, the presented supramolecular polymers display unique material properties because of the reversible nature of the H-bonding interactions between the polymer chains, allowing reversible change of the material properties by external stimuli like heat or dilution. Consequently, it is possible to prepare materials that combine the mechanical properties of conventional macromolecules with the low melt viscosity of organic compounds. The presence of 4H-units in the polymer backbone is strongly beneficial, because the materials are easier to synthesize and/or result in superior material properties as compared to polymers comprising 4H-units that have been disclosed previously, such as 4H-units grafted on polymers or 4H-units attached to the end groups of polymer chains.

SUMMARY OF THE INVENTION

The invented supramolecular polymers comprise quadruple hydrogen bonding units within the polymer backbone, wherein at least a monomer comprising a 4H-unit is incorporated in the polymer backbone via at least two reactive groups up to four reactive groups, preferably two to three and most preferably two reactive groups, provided that the 4H-units are not covalently incorporated in the polymer backbone through one or more silicon-carbon bonds. By the term "not covalently incorporated" it is meant that the 4H-unit is not attached to the polymer backbone by a silicon-carbon bond or by a linking moiety comprising a silicon-carbon bond.

It is even more preferred according to this invention that the invented supramolecular polymers comprise quadruple hydrogen bonding units within the polymer backbone, wherein at least a monomer comprising a 4H-unit is incorporated in the polymer backbone via at least two reactive groups up to four reactive groups, preferably two to three and most preferably two reactive groups, with the proviso that the 4H-units are not covalently incorporated in the polymer backbone through one or more silicon-carbon bonds and with the proviso that the following group of supramolecular polysiloxanes is excluded: polysiloxanes having the following general formulae (3a) or (3b):

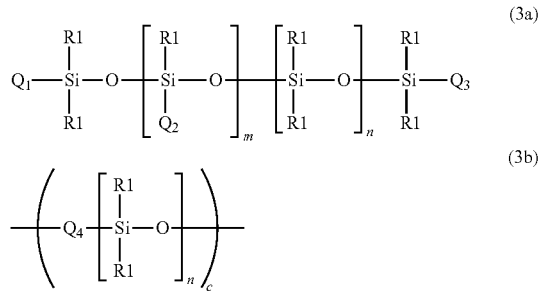

in which the radicals R1, that may be identical or different, are selected from substituted and unsubstituted monovalent non-aromatic ethylenically free $C_1$-$C_{20}$ hydrocarbon radicals, or are selected from aromatic radicals;

$Q_1$ and $Q_2$ and $Q_3$ are equal and denote one or more structural elements that are capable of forming at least four hydrogen bridges (also referred to as 4H-unit) and that are attached via a linker through a silicon-carbon bond to the polymer; or $Q_1$ and $Q_3$ are equal and denote one or more 4H-units attached via a linker through a silicon-carbon bond to the polymer and $Q_2$ is defined as R1; or $Q_1$ denotes one or more 4H-units attached via a linker through a silicon-carbon bond to the polymer and $Q_2$ and $Q_3$ are defined as R1: or $Q_2$ denotes one or more 4H-units attached via a linker through a silicon-carbon bond to the polymer and $Q_1$ and $Q_3$ are equal and are defined as R1; and $Q_4$ is a 4H-unit having two linkers that are attached through a silicon-carbon bond to the polymer chain, and m, n and c are integers such that the mean molecular weight of the polysiloxane ranges from 500 to 250000.

According to the present invention, the synthesis of the supramolecular polymers involves reaction of a monomeric unit (a) that comprises a (precursor of a) 4H-element and that comprises at least two reactive groups up to four reactive groups, preferably two to three and most preferably two reactive groups, with macromonomeric unit (b), preferably having a number average molecular weight of at least about 100 to about 100000. Different types of monomeric units (a) and macromolecular units (b) can be used in one synthetic procedure; several macromolecular units (b) can be employed wherein the macromolecular units (b) are for example of different chemical nature and/or of different molecular weight.

In the first embodiment of the present invention, the macromonomeric unit (b) comprises at least two complementary reactive groups up to six complementary reactive groups, preferably two to three complementary reactive groups and most preferably two complementary reactive groups, and is chain extended by reaction with monomer (a) having at least two to four reactive groups, preferably two to three reactive groups and most preferably two reactive groups. In this patent application the terms "reactive group" and "complementary reactive group" are used interchangeably to indicate reactive groups that are present in monomeric units and macromonomeric units. In this patent application complementary reactive groups are to be understood as reactive groups that are capable to form, preferably covalent, bonds under conventional reaction conditions as will be apparent to a person skilled in the art. Examples of reactive groups that are complementary reactive are carboxyl and hydroxyl groups that can form an ester group, carboxyl and amine groups that can form an amide group, hydroxyl groups that can form an ether group etc. However, as will be apparent to those skilled in the art, other modes of molecular bonds, e.g. ionic bonds or coordinative bonds, are within the scope of the present invention.

The resulting polymers (c) of the invention have the following general structure:

$$\{(a)_p - (b)_q\}_v$$

wherein:
(a) is a monomeric unit that comprises a (precursor of a) 4H-element;
(b) is a macromonomeric unit;
(a) and (b) are, preferably covalently, connected in the polymer backbone;
p and q indicate the total number of units of (a) and (b) in the polymer backbone;
p is 1 to 100, preferably 1 to 50 and most preferably 1 to 10;
q is 0 to 20, preferably 1 to 50 and more preferably 1 to 20;
v is the number of repeating units of the connected monomeric units (a) and the connected macromonomeric units (b);
macromonomeric unit (b) has a number average molecular weight of at least about 100 to about 100000, preferably about 500 to about 50000 and more preferably about 500 to about 30000; and
polymer (c) has a number average molecular weight of about 2000 to about 80000;
provided that the 4H-units are not covalently incorporated in the polymer backbone through one or more silicon-carbon bonds.

According to the invention, polymer (c) can be a homopolymer (q=0). However, it is preferred that the units (a) and (b) are both present. Units (a) and (b) can be randomly distributed along the polymer chain but can also be alternating (i.e. that a segmented polymer is obtained). According to the present invention, it is preferred that the polymer is an alternating copolymer.

According to the second embodiment of the present invention, the macromonomeric unit (b) is a polymer of higher number average molecular weight, preferably at least about 20000 to about 100000, that can be redistributed using monomer (a). The resulting polymers (c') have now the general (segmented) structure:

$$\{(a)_p-(b')_q\}_w$$

wherein
(a) is a monomeric unit that comprises a (precursor of a) 4H-element;
(b') is a fragmented part of the original polymer (b);
(a) and (b') are, preferably covalently, connected in the polymer backbone;
p and q indicate the total number of units of (a) and (b) in the polymer backbone;
p is 1 to 100, preferably 1 to 50 and most preferably 1 to 10;
q is 0 to 20, preferably 1 to 50 and more preferably 1 to 20;
w is the number of repeating units of the connected monomeric units (a) and the connected macromonomeric units (b');
macromonomeric unit (b') has a number average molecular weight of at least about 50 to about 20000, preferably about 50 to about 10000; and
the polymer (c') has a number average molecular weight of about 2000 to about 80000;
provided that the 4H-units are not covalently incorporated in the polymer backbone through one or more silicon-carbon bonds. As will be apparent to the person skilled in the art, the polymer (c') comprises fragmented parts (b') that may have a different number average molecular weight and/or a different molecular structure, i.e. that not all fragmented parts (b') need to be identical.

The number average molecular weight of the polymers according to the present invention are determined by size-exclusion chromatography (SEC) also known in the art as gel permeation chromatography (GPC) using polystyrene standards.

The supramolecular polymers according to the present invention comprise self-complementary quadruple hydrogen bonding units (4H-elements or 4H-units) in the polymer backbone. The amount of 4H-units incorporated in the polymer backbone is preferably about 33 to about 66 mol %, based on the total amount of moles of (a) and (b) or (a) and (b'), more preferably about 40 to about 60 mol %, and most preferably about 44 to about 55 mol %.

According to the first embodiment of the present invention, the synthesis of the supramolecular polymers according to the invention involves reaction of a monomeric unit (a) that contains a (precursor of a) 4H-element and that bears at least two reactive groups up to four reactive groups, preferably two to three reactive groups and most preferably two reactive groups, with a macromonomeric unit (b) having at least two complementary reactive groups up to six complementary reactive groups, preferably two to three complementary reactive groups and more preferably two complementary reactive groups, and wherein the macromonomeric unit (b) has a number average molecular weight of at least about 100 to about 100000. In this first embodiment, the macromonomeric unit (b) is chain extended by reaction with monomer (a).

According to the second embodiment of the present invention, the macromonomeric unit (b) is a polymer of higher number average molecular weight, preferably at least about 20000 to about 100000, that can be redistributed using monomer (a), wherein the monomeric unit (b) has a number average molecular weight of at least about 50 to about 20000.

DETAILED DESCRIPTION OF THE INVENTION

Description of the Monomeric Unit (a)

Monomeric unit (a) comprises a (precursor of a) 4H-unit and several reactive groups linked to this unit, wherein the reactive groups can form chemical bonds, preferably covalent bonds, upon reaction with macromonomeric unit (b). In general, monomeric unit (a) can be represented by the formulae (III) and (IV),

  (III)

  (IV)

wherein:
4H represents a structural element (4H):
4H* represents a precursor of the structural element (4H):
$F_i$ represents a reactive group linked to the 4H-unit or 4H*-unit; and
r represents the number of reactive groups connected to the (precursor of the) structural element (4H) and is within the range of 1-4.

Hence, the 4H-unit may comprise up to four reactive groups $F_1$, $F_2$, $F_3$ and $F_4$, provided that the 4H-unit comprises at least two of such reactive groups.

According to the present invention, r can be from 1 to 4. According to the present invention, r is preferably 2 or 3 and most preferably 2.

According to the present invention, the monomeric unit (a) can preferably (r=2) be represented by the following formulae:

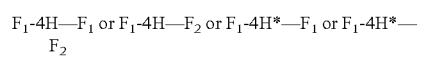

In general, the structural element that is capable of forming at least four hydrogen bridges (4H) has the general form (1') or (2'):

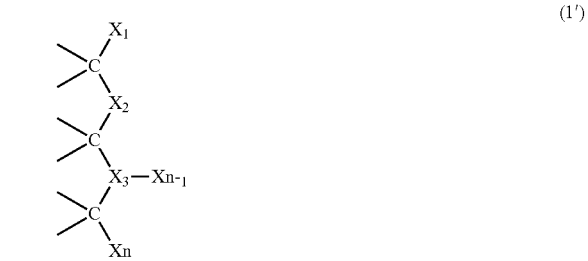 (1')

 (2')

If the structural element (4H) is capable of forming four hydrogen bridges which is preferred according to the invention, the structural element (4H) has preferably the general form (1) or (2):

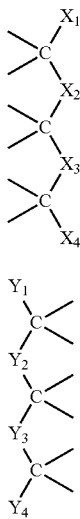

(1)

(2)

In all general forms shown above the C—$X_i$ and C—$Y_i$ linkages each represent a single or double bond, n is 4 or more and $X_1 \ldots X_n$ represent donors or acceptors that form hydrogen bridges with the H-bridge-forming unit containing a corresponding structural element (2) linked to them, with $X_i$ representing a donor and $Y_i$ an acceptor or vice versa. Properties of the structural element having general forms (1'), (2'), (1) or (2) are disclosed in U.S. Pat. No. 6,320,018 which for the US practice is incorporated herein by reference.

The structural elements (4H) have at least four donors or acceptors, preferably four donors or acceptors, so that they can in pairs form at least four hydrogen bridges with one another. Preferably the structural elements (4H) have at least two successive donors, followed by at least two acceptors, preferably two successive donors followed by two successive acceptors, preferably structural elements according to general form (1') or more preferably (1) with n=4, in which $X_1$ and $X_2$ both represent a donor and an acceptor, respectively, and $X_3$ and $X_4$ both an acceptor and a donor, respectively. According to the invention, the donors and acceptors are preferably O, S, and N atoms.

Molecules that can be used to construct the structural element (4H) are nitrogen containing compounds that are reacted with isocyanates, thioisocyanates or activated amines, or that are activated and reacted with primary amines, to obtain a urea or thiourea moiety that is part of the quadruple hydrogen bonding site. The nitrogen containing compound is preferably an isocytosine derivative (i.e. a 2-amino-4-hydroxy-pyrimidine derivative) or a triazine derivative, or a tautomer and/or enantiomer of these derivatives. More preferably, the nitrogen containing compound is an isocytosine derivative having a proton or aliphatic-substituent containing a functional group in the 5-position and an alkyl-substituent in the 6-position, most preferably 2-hydroxy-ethyl or propionic acid ester in the 5-position and methyl in the 6-position, or hydrogen in the 5-position and methyl in the 6-position. The isocyanates or the thioisocyanates can be monofunctional isocyanates or monofunctional thioisocyanates or bifunctional diisocyanates or bifunctional thioisocyanates (for example alkyl or aryl (di)(thio)isocyanate(s)).

According to the invention, monomer (a) that contains the structural element (4H) is particularly suitably represented in the compounds having the general formulae (3) or (4), and tautomers and/or enantiomers thereof (see below). Monomer (a) that contains a precursor of the structural element (4H), i.e. (4H*), is particularly suitably represented in the compounds having the general formulae (5) or (6). The X in formulae (4) and (6) is preferably a nitrogen atom, but it can also be a carbon atom with attached R4-group.

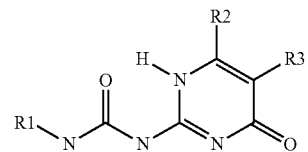

(3)

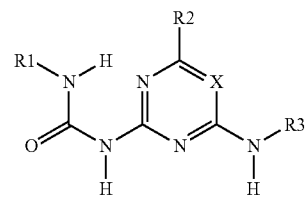

(4)

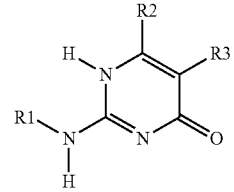

(5)

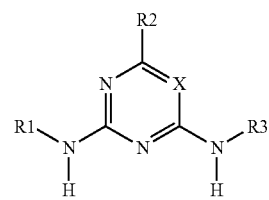

(6)

R1, R2, R3 and R4 may be hydrogen or all kinds of shorter or longer chains, for example saturated or unsaturated, branched, cyclic or linear alkyl chains, aryl chains, alkaryl chains, arylalkyl chains, ester chains, ether chains and any chain of atoms used in traditional polymer chemistry, whether or not substituted with all kinds of functional groups such as esters, ethers, ureas or urethanes.

It is preferred according to the present invention that the shorter or longer chains are saturated or unsaturated, branched, cyclic or linear alkyl chains, aryl chains, alkaryl chains, alkylaryl chains, ester chains or ether chains.

Preferably, "saturated or unsaturated, branched, cyclic or linear alkyl chains" denote a $C_1$-$C_{10}$ alkylene group.

"Aryl chains" preferably denote a $C_6$-$C_{12}$ arylene group.

"Alkaryl chains" and "alkylaryl chains" preferably denote a $C_7$-$C_{12}$ alkaryl group and a $C_7$-$C_{12}$ alkylaryl group, respectively.

"Ester chains" preferably denote a polyester obtained by ring opening polymerisation of $C_4$-$C_8$ lactones or dilactides or glycolides having the general formula:

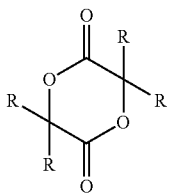

wherein the R groups are independently selected from the group consisting of linear or branched $C_1$-$C_6$ alkyl groups. However, it is preferred that for "ester chains" the R groups are independently selected from hydrogen atoms and methyl groups.

"Ether chains" preferably denote a polyether chain comprising ethylene oxide and/or propylene oxide, wherein the polyether chain is represented by the formula:

wherein $R^{**}$ can be a hydrogen atom or a methyl group and w is in the range of 10-100.

Preferably, if any one of R1-R4 comprises a reactive group ($F_i$) and is therefore a linking moiety, said linking moiety is hydrogen or a $C_1$-$C_{12}$ straight chain or branched alkylene group or a $C_6$-$C_{12}$ arylene, a $C_7$-$C_{12}$ alkarylene or a $C_7$-$C_{12}$ arylalkylene group, wherein the alkylene, arylene, alkarylene or arylalkylene group may be substituted with other groups or may contain cyclic groups as substituent or in the main chain. Examples of such groups are methylene, ethylene, propylene, tetramethylene, pentamethylene, hexamethylene heptamethylene, octamethylene, nonamethylene, 1,6-bis(ethylene)cyclohexane, 1,6-bismethylene benzene, etc. The alkylene, arylene, alkarylene or arylalkylene groups may be interrupted by heteroatoms, in particular heteroatoms selected from the group consisting of oxygen, nitrogen, and sulphur.

However, according to the invention, it is even more preferred that the structural elements (4H) or (4H*) in the compounds (3) and (4) or (5) and (6), respectively, are connected to two reactive groups ($F_i$) via one or two R groups of the series R1-R4 with the other R-group(s) representing a random side chain or hydrogen atoms.

Hence, for formula (3), the structural element (4H) is preferably connected to a reactive group ($F_1$) via R1 and a reactive group ($F_1$) or ($F_2$) via R2, whereas R3 is a random side chain or a hydrogen atom; or the structural element (4H) is connected to a reactive group ($F_1$) via R1 and to a reactive group ($F_1$) or ($F_2$) via R3, whereas R2 is a random side chain or a hydrogen atom; or the structural element (4H) is bonded to two reactive groups ($F_i$) both via $R_1$, whereas R2 and R3 are random side chains or hydrogen atoms. According to the invention, the random side chain is preferably a $C_1$-$C_7$ alkyl group, most preferably 2-ethylpentyl or methyl. According the present invention, the term "alkyl" when used in connection with the random side chain encompasses linear, branched and cyclic alkyl groups but the random side chain is preferably a linear alkyl group (to indicate that the reactive groups ($F_i$) may be different, they are specified as ($F_1$) or ($F_2$)).

Most preferably, for formula (3), one reactive group ($F_1$) is connected via R1 and one reactive group ($F_1$) or ($F_2$) is connected via R3, while R2 is a random side chain as defined above.

More preferably, for formula (5), the structural element (4H*) is connected to a reactive group ($F_1$) via R1 and a reactive group ($F_1$) or ($F_2$) via R2, whereas R3 is a random side chain as defined above or a hydrogen atom, or the structural element (4H*) is connected to a reactive group ($F_1$) via R1 and to a reactive group ($F_1$) or ($F_2$) via R3, whereas R2 is a random side chain as defined above or a hydrogen atom. Most preferably, for formula (5), one reactive group ($F_1$) is connected via R1 and one reactive group ($F_1$) or ($F_2$) is connected via R3, while R2 is a random side chain as defined above.

The reactive groups ($F_i$) can comprise any functional group. Preferred functional groups, however, are a hydroxy, carboxylic acid, carboxylic ester (including activated ester), acid halide, isocyanate (including blocked isocyanate), thioisocyanate, primary amine (including activated amine), secondary amine (including activated amine), vinyl, (meth)acrylate, thiol or halogen group.

In this patent application, "hydroxy" denotes a —OH group.

A "carboxylic acid" denotes a —C(O)OH group.

A "carboxylic ester" denotes a —C(O)OR group, wherein R is selected from the group consisting of $C_1$-$C_6$ alkyl, $C_6$-$C_{12}$ aryl, $C_7$-$C_{12}$ alkaryl and $C_7$-$C_{12}$ alkylaryl groups, wherein the alkyl groups may be linear, branched or cyclic.

An "acid halide" denotes a —C(O)X group, wherein X is a chlorine atom, a bromine atom or a iodine atom. Preferably X is a chlorine or a bromine atom.

An "isocyanate" denotes a —NCO group.

A "blocked isocyanate" denotes a —NHC(O)OR* group, wherein R* is a good leaving group. Suitable examples of good leaving groups are phenol-derivatives phenol and thiophenol derivatives, ester derivatives such as the methyl ester of hydroxy-benzoic acid, alcohol derivatives such as 2-ethyl-hexyl-alcohol and t-butyl-alcohol, oxime derivatives such as methyl-ethyl ketoxime, imidazole groups, caprolactam groups and hydroxy-succinimide groups.

A "thioisocyanate" denotes a —NCS group.

An "blocked thioisocyanate" denotes a —NHC(S)OR* group, wherein R* is a good leaving group as indicated for "blocked isocyanate".

A "primary amine" denotes a —NH$_2$ group.

A "secondary amine" denotes a —NHR group, wherein R is as defined above for "carboxylic ester".

An "activated amine" denotes a —C(R)=NOH group (that can be converted into an amine group via the Beckmann rearrangement), a —C(O)N$_3$ group (that can be converted into an amine group via the Curtius rearrangement), a —C(O)NH$_2$ group (that can be converted into an amine group via the Hofmann rearrangement), a —NHC(O)R group wherein R is as defined above for "carboxylic ester" including cyclic groups such as caprolactam, a heterocyclic five or six membered group comprising 1-3 heteroatoms selected from the group consisting of O, S and N such as imidazole. According to the present invention, the "activated amine" is preferably caprolactam or imidazole.

A "vinyl" denotes a —CR$^a$=CR$^b{}_2$ group, wherein R$^a$ and R$^b$ are independently selected from the group consisting of hydrogen atoms and the groups defined for R.

A "(meth)acrylate" denotes a —C=C(R$^c$)—C(OH)R group, wherein R$^c$ is a hydrogen atom or a methyl group and wherein R is as defined above or a hydrogen atom.

A "thiol" denotes a —SH group.

A "halogen" denotes a —X group, where X is chlorine, bromine or iodine.

Preparation of Monomeric Units (a)

According to the invention, the monomeric units (a) are preferably prepared by the following methods (see also the figures).

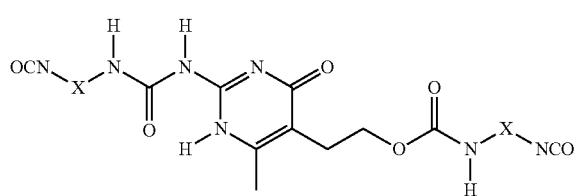

Preferred First Method, with X Derived from the Applied Di-Isocyanate

In the first method, according to formula (3), monomeric unit (a) is obtained by reaction of an isocytosine derivative having an alcohol function in the R2 or R3 group with 2 equivalents of a diisocyanate derivative represented by the formula:

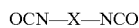

wherein X is a linear, branched or cyclic $C_1$-$C_{16}$ alkyl group, a $C_6$-$C_{16}$ aryl group, a $C_7$-$C_{16}$ alkaryl or a $C_7$-$C_{16}$ alkylaryl group.

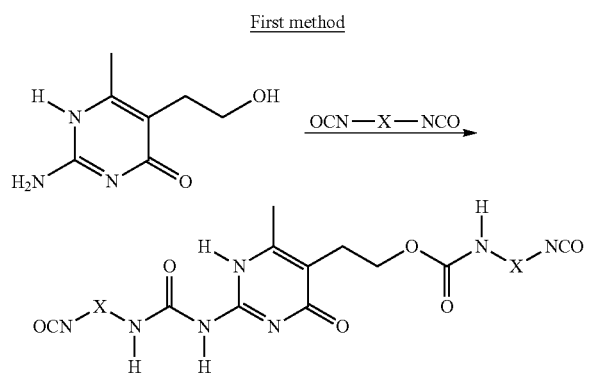

Preferably, the isocytosine-derivative is a 6-alkyl-isocytosine with an alcohol functionality in the R3 group, wherein the alkyl group may be branched or linear and contains one to seven carbon atoms, more preferably 5-(2-hydroxyethyl)-6-alkyl-isocytosine, wherein the alkyl group may be branched or linear and contains one to seven carbon atoms, and most preferably 5-(2-hydroxyethyl)-6-methyl-isocytosine. Examples of suitable diisocyanates that can be used in this invention are:
1,4-diisocyanato-4-methyl-pentane,
1,6-diisocyanato-2,2,4-trimethylhexane,
1,6-diisocyanato-2,4,4-trimethylhexane,
1,5-diisocyanato-5-methylhexane,
3(4)-isocyanatomethyl-1-methylcyclohexyl isocyanate,
1,6-diisocyanato-6-methyl-heptane,
1,5-diisocyanato-2,2,5-trimethylhexane,
1,7-diisocyanato-3,7-dimethyloctane,
1-isocyanato-1-methyl-4-(4-isocyanatobut-2-yl)-cyclohexane,
1-isocyanato-1,2,2-trimethyl-3-(2-isocyanato-ethyl)-cyclopentane,
1-isocyanato-1,4-dimethyl-4-isocyanatomethyl-cyclohexane,
1-isocyanato-1,3-dimethyl-3-isocyanatomethyl-cyclohexane,
1-isocyanatol-n-butyl-3-(4-isocyanatobut-1-yl)-cyclopentane.
1-isocyanato-1,2-dimethyl-3-ethyl-3-isocyanatomethyl-cyclopentane,
3(4)-isocyanatomethyl-1-methylcyclohexyl isocyanate (IMCI),
toluene diisocyanate (TDI),
methylene diphenyl diisocyanate (MDI),
methylene dicyclohexane 4,4-diisocyanate,
isophorone diisocyanate (IPDI), hexane diisocyanate (HDI).

More preferably, the diisocyanate is IPDI, HDI, MDI, TDI, 1,6-diisocyanato-2,2,4-trimethylhexane, 1,6-diisocyanato-2,4,4-trimethylhexane or methylene dicyclohexane 4,4-diisocyanate.

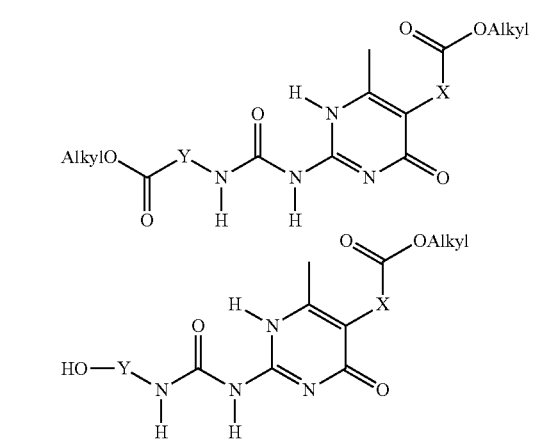

Preferred Second and Third Methods, X and Y are Short Alkylene Spacers and the Alkyl Esters are Preferably Methyl or Ethyl In a second method, according to formula (3), monomeric unit (a) is obtained by reaction of a 6-alkyl-isocytosine bearing a $C_1$-$C_6$ carboxylic ester in the R3 group with a bifunctional compound that contains an isocyanate or activated amine function and another function.

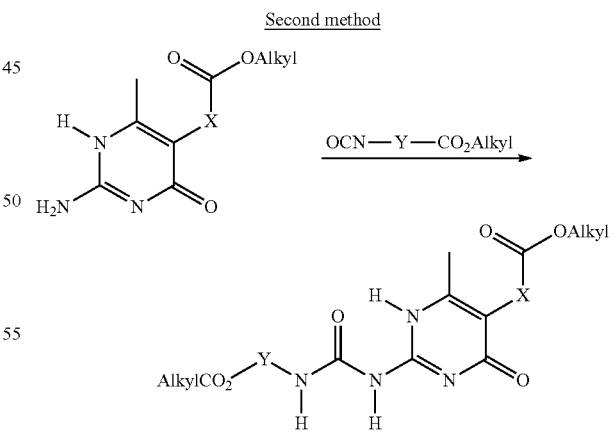

Preferably, the isocytosine derivative is 5-(3-alkyl-propionate)-6-methyl-isocytosine as shown in the reaction equation depicted above and the bifunctional compound is an isocyanate with $C_1$-$C_6$ carboxylic alkyl ester function, wherein the alkyl group may be branched or linear and contains one to seven carbon atoms. Suitable examples of such bifunctional compounds are the ethyl ester of 1-isocyanato acetic acid, the ethyl ester of 3-isocyanato propionic acid, or the ethyl ester of 6-isocyanato hexanoic acid.

In a third method, according to formula (3), monomeric unit (a) is obtained by reaction of a 6-alkyl-isocytosine bearing a $C_1$-$C_6$ carboxylic ester in the R3 group and a (masked) isocyanato-function in the R1-group with a bifunctional compound that contains a primary amine and another function, preferably a $C_1$-$C_6$ carboxylic alkyl ester or alcohol function.

Third method (preferred)

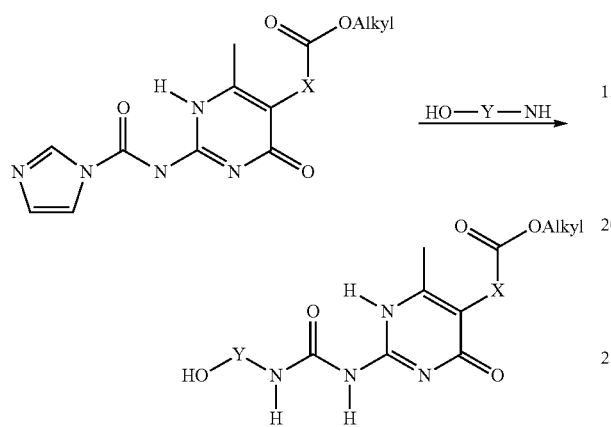

Preferably, as is schematically shown in the reaction equation depicted above, the isocytosine derivative is 1-carboimidazole-5-(3-ethyl-propionate)-6-methyl-isocytosine, and the bifunctional compound is an alpha-amino-omega-alcohol alkane wherein the alkylene moiety comprises 1-16 carbon atoms and wherein the alkylene moiety may be linear or branched, or an alpha amino omega carboxylic ester alkane wherein the alkylene moiety comprises 1-16 carbon atoms and wherein the alkylene moiety may be linear or branched and wherein the ester group is derived from a a $C_1$-$C_6$ alcohol.

In these second and third methods, X en Y independently denote short alkylene spacers, wherein the alkylene group is a $C_1$-$C_6$ alkylene group that may be linear or branched and wherein the alkyl groups of the ester moieties independently denote linear or branched $C_1$-$C_6$ alkyl groups, preferably methyl or ethyl groups.

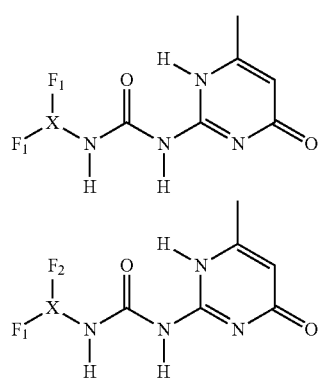

Preferred Fourth Method, X is a Short Alkylene Spacer, $F_1$ and $F_2$ are Alcohols or Carboxylic Esters In a fourth method, according to formula (3), monomeric unit (a) is obtained by first activating an isocytosine, preferably 6-methyl isocytosine or 6-(2-ethyl-pentyl)-isocytosine, with a di-substituted carbonyl compound, such as for example carbonyldiimidazole (CDI), followed by reaction of the resulting 1-carboimidazole-isocytosine with an amine-compound that contains two additional functions, preferably carboxylic ester(s) and/or alcohol(s).

Examples of the amine-compound are glutaric acid, aspartic acid, 2-amino-2-methyl 1,3-propanediol, 2-amino-1,3-propanediol. In this fourth method X is defined above and F1 and F2 are independently —OH groups or ester groups —C(O)OR wherein R is a linear or branched $C_1$-$C_6$ alkyl group Fourth method (preferred)

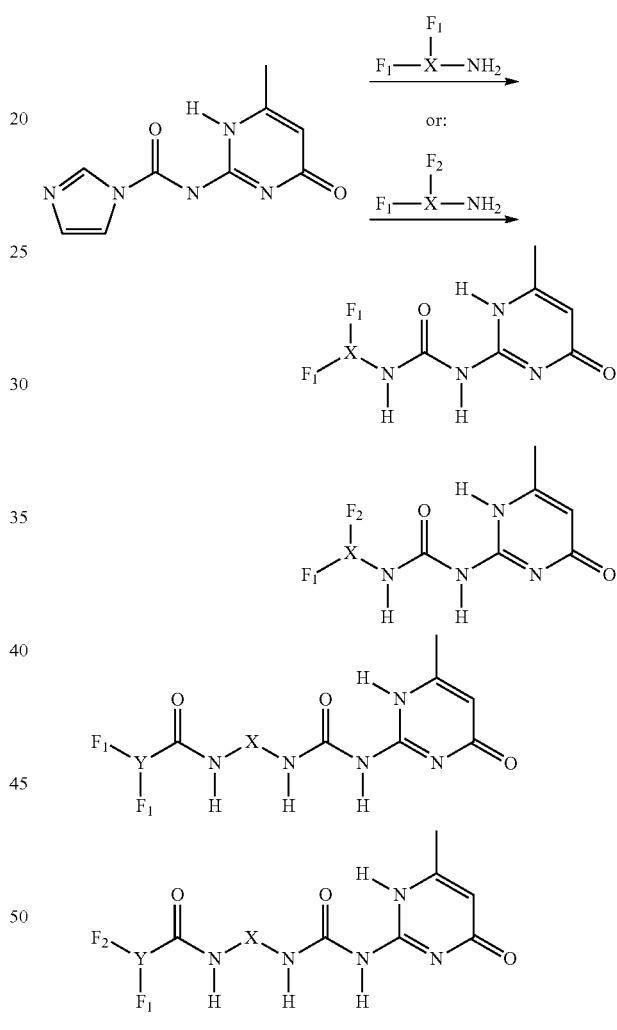

Preferred Fifth Method, X is an Alkylene Spacer, F1 and F2 are Alcohols or Carboxylic Esters and Y is a Spacer In a fifth method, according to formula (3), monomeric unit (a) is obtained by reacting an isocytosine, preferably 6-methyl-isocytosine with one equivalent of a diisocyanate OCN—X—CNO defined above. The product bearing one isocyanate function is then reacted with an amine-compound or alcohol-compound that bears two further functions $F_1$—Y—$F_1$ or $F_1$—Y—$F_2$. An example of such compound is bis(2-hydroxyethyl)amine. According to this fifth method, $F_1$, $F_2$, X and Y are defined as above.

Fifth method

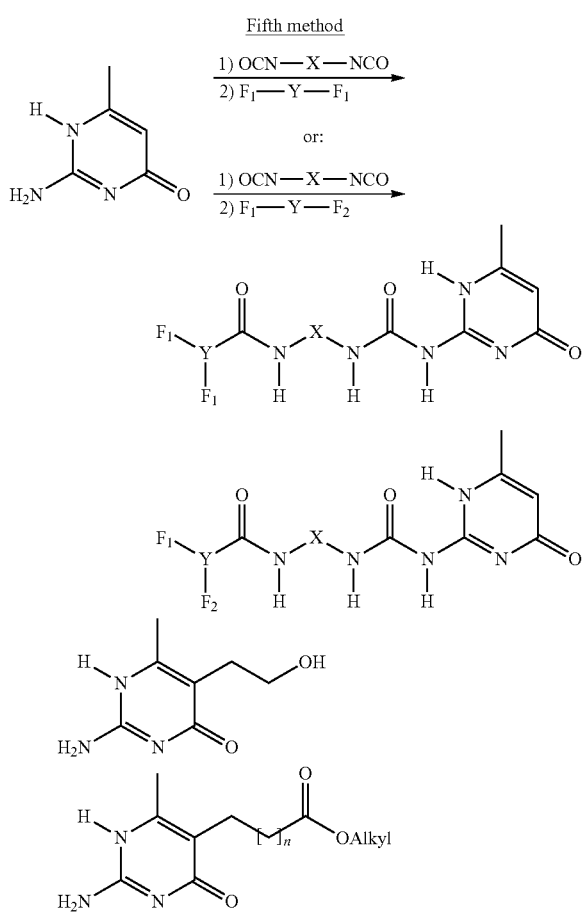

Preferred Sixth Method, n is 0 or 1, Alkyl is Preferably Methyl or Ethyl

In a sixth method, according to formula (5), monomeric unit (a) is an isocytosine with an alcohol or carboxylic ester function in the R2 or R3 group, more preferably in the R3 group, most preferably monomeric unit (a) is 5-(2-hydroxyethyl)-6-methyl-isocytosine or 5-(3-ethyl-propionate)-6-methyl-isocytosine. The ester function is preferably derived from a linear or branched $C_1$-$C_6$ alcohol.

Description of the Macromonomeric Unit (b)

Chain Extension Approach

Macromonomeric unit (b) can be any functional polymer or oligomer and can be represented in the following schematic form:

$$P\text{—}(F_i)_s$$

where P represents the polymer chain, $F_i$ represents the functional or complementary reactive groups in the macromonomeric unit and s represents the number of these groups in the macromonomer. The complementary reactive or functional groups ($F_i$) are defined as previous for monomer (a), s is 1 or more, preferably 2 to 6, more preferably 2 to 3, most preferably 2, with the proviso that the complementary group is complementary reactive with another $F_i$ of monomeric unit (a).

In this preferred embodiment of the present invention, the macromonomeric unit (b) has a discrete low number of reactive end groups, most preferably two, so the macromonomeric unit (b) can schematically be written as:

$$F_2\text{—}P\text{—}F_2 \text{ or } F_1\text{—}P\text{—}F_2$$

wherein P represents any polymer backbone, such as a polyether, polyester, polyamide, polyacrylate, polymethacrylate, polyolefin, hydrogenated polyolefin, polycarbonate, or the like. P can also represent copolymers of any kind. According to a preferred embodiment of the invention, P is selected from the group consisting of polyether, polyester, polycarbonate or hydrogenated polyolefin. In this approach, the number average molecular weight of the polymer P is preferably in the range from 100 to 100000, more preferably from 100 to 30000, even more preferably 500 to 30000, most preferably from 500 to 5000.

Preferably, macromonomeric unit (b) is a polymer with two hydroxyl end-groups. Examples are polyetherdiols having a polyoxyalkylene structure and hydroxyl end-groups, such as polyethylene glycol, polypropylene glycol, poly(ethylene-co-propylene)glycol, polytetramethylene glycol, or polyesterdiols, such as polycaprolactonediol, diol end-capped poly(1,4-butylene adipate), diol end-capped poly(1,4-butylene glutarate), or polyolefinediols, such as hydroxyl functionalized polybutadiene, hydroxyl functionalized poly(ethylene-butylene), or polycarbonates such as poly(1,3-propanediol carbonate)glycol or poly(1,6-hexanediol carbonate) glycol, or polyamide diols.

Another preferred macromonomeric unit (b) is a polymer with primary amine end-groups. Examples are Jeffamines® (polyoxyalkylenea amines produced and marketed by Huntsman) and aliphatic polyamides.

Another preferred macromonomeric nit (b) is a polymer with isocyanate end groups. Examples are polymers with hydroxyl end groups (see above) that have been treated with two equivalents of a diisocyanate, preferably isophorone diisocyanate (IPDI).

Yet another preferred macromonomeric unit (b) has vinyl end groups.

Polymer Redistribution Approach

In this embodiment of the invention, the macromonomeric unit (b) has a high number of functional groups in the main chain of the polymer. The macromonomeric unit (b) is a polymer that can be written as:

P where P represents polymers or copolymers of any kind, provided they can be submitted to redistribution reactions with a monomer. These redistribution reactions are well known to the skilled person in the art. Reference is for example made to Korshak, V. V. and Vasnev, V. A., Comprehensive Polymer Science; Pergamon Press; London, 1989; Vol. 5, page 131. In this approach, the number average molecular weight of P is in the range from 5000 to 100000, more preferably from 10000 to 80000.

Examples for P that are well known in the art are polyesters obtained by ring-opening polymerization (ROP) of cyclic lactones, glyclides, lactides or mixtures thereof such as polycaprolactone, polylactide, poly(lactide-c-glycolide), aliphatic polyesters obtained by AA-BB type polycondesation, such as poly(2-methyl-1,3-propylene adipate), or aromatic polyesters such as poly(ethylene terephthalate). According to the invention, preferred examples for P are polyesters and polycarbonates.

Description of the Copolymerization and of the Polymer

The polymers presented in this invention are obtainable by reacting or copolymerizing the disclosed monomeric unit (a)

with the disclosed macromonomeric unit (b), either via the chain extension or the redistribution approach, to a polymer (c). The reactive groups ($F_i$) in monomeric unit (a) and the complementary reactive groups ($F_i$) in macromonomeric unit (b) must be complementary. In this patent application complementary reactive groups are to be understood as reactive groups that form, preferably covalent, bonds under conventional reaction conditions as will be apparent to a person skilled in the art. Examples for complementary reactive groups are carboxyl and hydroxyl groups that can form an ester group, carboxyl and amine groups that can form an amide group, hydroxyl groups that can form an ether group etc. Preferred combinations of reactive groups and complementary reactive groups (and vice versa) are:

reactive group=—OH; complementary reactive group=—C(O)OR wherein R is selected from the group consisting of hydrogen atoms, $C_1$-$C_6$ alkyl, $C_6$-$C_{12}$ aryl, $C_7$-$C_{12}$ alkaryl and $C_7$-$C_{12}$ alkylaryl groups, wherein the alkyl groups may be linear, branched or cyclic, or wherein OR represents a halogen atom selected from the group consisting of Cl, Br and I. Suitable examples for R are pentafluorophenyl, 4-nitrophenyl or 2-nitrophenyl.

reactive group is primary or secondary amine of the formula —NHR, wherein R is selected from the group consisting of hydrogen atoms, $C_1$-$C_6$ alkyl, $C_6$-$C_{12}$ aryl, $C_7$-$C_{12}$ alkaryl and $C_7$-$C_{12}$ alkylaryl groups, wherein the alkyl groups may be linear, branched or cyclic; or wherein the primary or secondary amine is of the formula HRN—(CH$_2$—CH$_2$X)$_n$—H wherein R is as defined herein above, X is independently selected from the group consisting of O, S and NH and is preferably O, and wherein n is 1-10; complementary reactive group is —NCO.

The polymer product (c) is a segmented copolymer that has structural elements (4H) in the polymer backbone. For the chain extension approach, polymer (c) can be written as, $$\{(a)_p\text{-}(b)_q\}_v$$

wherein v is the number of repeating units of the connected monomeric unit (a) and the connected macromonomeric unit (b).

For the polymer redistribution approach polymer (c') can be written as, $$\{(a)_p\text{-}(b')_q\}_w$$

where (b') represents the incorporated and fragmented parts of macromonomer unit (b), and w is the number of repeating units of the connected monomeric unit (a) and fragments (b').

The production of polymers (c) and (c') may involve any kind of polymerization procedure or process known in traditional polymerization. Solution, bulk, suspension, and other types of polymerizations may be used; one-pot procedures or a sequence of (polymerization) reactions may be used to produce polymers (c) and (c').

The resulting polymers (c) and (c') have an number average molecular weight in between 2000 and 80000.

Chain Extension Polymerization

In this embodiment of the invention (i.e. the macromonomeric unit (b) is chain extended) the following sets of monomeric unit (a) and macromonomeric unit (b) are polymerized:

$F_1$-4H—$F_1$ and $F_3$—P—$F_3$ $F_1$-4H—$F_2$ and $F_3$—P—$F_3$ $F_1$-4H*—$F_1$ and $F_3$—P—$F_3$ $F_1$-4H*—$F_2$ and $F_3$—P—$F_3$ where the couple $F_1$-$F_3$ and the couple $F_2$-$F_3$ are complementary reactive groups (as defined above), enabling covalent bond formation upon reaction between the two complementary reactive groups. The complementary reactive groups $F_1$, $F_2$ and $F_3$ can be any functional group, examples have been described previously (for $F_i$). However, according to the invention it is preferred that $F_1$, $F_2$ and $F_3$ are an isocyanate, blocked isocyanate, alcohol, carboxylic acid or a derivative thereof or primary or secondary amine as defined above.

In a particular embodiment of the invention, monomeric unit (a) contains two isocyanate functions ($F_1$-4H—$F_1$, with $F_1$=isocyanate) and is reacted with macromonomeric unit (b) having two alcohol or two amino functions (i.e. $F_3$-4H—$F_3$, $F_3$=hydroxy or amine). In another particular embodiment of this invention the structural element (4H) is formed in situ during polymerization by reaction of an isocytosine containing an alcohol-group (i.e. $F_1$-4H*—$F_2$, with $F_1$ is amine and $F_2$ is alcohol) with a macromoneric unit (b) having two isocyanato functions (i.e. $F_3$—P—$F_3$, $F_3$=isocyanato).

In another preferred embodiment of this invention monomeric unit (a) containing two carboxylic acid derivative functions (i.e. $F_1$-4H—$F_1$ with $F_1$=carboxylic acid derivative) is reacted with macromonomeric unit (b) having two alcohol or two amine functions (i.e. $F_3$—P—$F_3$, $F_3$=hydroxy or amine).

According to the invention, more than one type of monomeric unit (a) and/or type of macromonomeric unit (b) can be used in the polymerization reaction. Examples of this inclusion are:

(i) The use of two or more macromonomeric units (b) that differ in number average molecular weight and/or in molecular structure.

(ii) The use of monofunctional species ('stopper'-molecules) of monomeric unit (a) or macromonomeric unit (b); in formulae these 'stopper'-molecules can be denoted as: P—$F_1$ or 4H—$F_1$ or 4H*—$F_1$. The procedure of adding 'stopper' molecules is well known in the art (cf. for example Flory, P. J.; J. Am. Chem. Soc. 1942, Vol. 64, p. 2205), and enables the control of the molecular weight and of the end-groups in the polymer product (c). A particular 'stopper' molecule 4H—$F_1$ is 2-(3-(6-isocyanato-hexyl)-ureido-6-methyl-isocytosine.

(iii) The use of branching species of monomeric unit (a) or macromonomeric unit (b); in formulae these branched molecules can be denoted as: P—$(F_i)_u$ or 4H—$(F_i)_u$ or 4H*—$(F_i)_u$, with u being 3 or more up to 6, preferably 3. The use of branched molecules enables the control of branching in and of molecular weight of the polymer product (c).

As will be apparent to those skilled in the art, in the following formula representing the macromonomeric unit (b):

P—$(F_i)_s$ s may be zero (redistribution reactions) or s may be 1 if monofunctional species ('stopper'-molecules) of monomeric unit (a) or macromonomeric unit (b) are used.

According to the invention, any molar ratio between monomeric unit (a) and macromonomeric unit (b) can be used in the polymerization reaction. This enables the control of the number average molecular weight of the product polymer (c), and of the average amount of structural elements (4H) per polymer chain in polymer (c). Preferred molar ratios between monomeric unit (a) and macromonomeric unit (b) range from 1:2 to 2:1, more preferably ratios from 2:3 to 3:2 are used, and most preferably the molar ratio is 4:5 to 5:4.

The Polymer Redistribution Reaction

In another preferred embodiment of the invention the following sets of monomeric units (a) and macromonomeric units (b) are reacted (i.e. the polymer redistribution reaction):

$F_1$-4H—$F_1$ and P $F_1$-4H—$F_2$ and P

In redistribution, monomeric unit (a) is mixed and reacted with macromonomeric unit (b). During reaction, both reactive ends of monomeric unit (a) react with the chemical bonds in the polymer chain of macromonomeric unit (b), so that macromonomeric unit (b) is fragmented—to (b')—and a new polymer (c') with structural elements (4H) in its backbone is formed. Additionally, fragments of polymer (b) without 4H-units are formed.

The reactive groups $F_1$ and $F_2$ can be any functional group, examples have been described previously (for $F_i$). Particularly, $F_1$ and $F_2$ are hydroxy groups, primary or secondary amine groups, carboxylic acid groups or derivatives thereof, preferably carboxylic ester groups, or carbonates, while P is a polyester, polycarbonate, polyamide or copolymers of said polymers P. Preferably, the monomeric units comprise —OH groups as reactive groups whereas the polymer P comprises as complementary reactive groups a carboxylic acid, a carboxylic acid anhydride, a carboxylic halide (halide preferably Cl or Br), a carboxylic ester or an activated ester group as defined above; or the monomeric units comprise carboxyl ester groups as defined above whereas the polymer P comprise as complementary reactive groups a carboxylic acid, a carboxylic halide (halide preferably Cl or Br) or a carboxylic acid anhydride as defined above (carboxylic halides are herein defined as carboxylic acid halides of the formula —C(O)X wherein X is Cl, Br, or I, preferably Cl or Br; carboxylic anhydride are herein defined as —C(O)—O—(O)—C—).

The molar ratio between monomeric unit (a) and macropolymeric unit (b) is in between 3:1 and 10:1, more preferably in between 5:1 and 8:1. The number molecular weight of (b) is in between 20000 and 100000.

In a preferred embodiment of this invention redistribution takes place by transesterfication reactions between monomeric unit (a) wherein $F_1$ or $F_2$ is an alcohol, carboxylic acid, or carboxylic ester function and macromonomeric unit (b) is a polyester or a polycarbonate. The transesterfication can take place in the presence of catalysts well known in the art such as metal-based catalysts, for example titanium or tin compounds, or metal-free organic catalysts, for example DMAP or N-heterocyclic carbenes. Or the transesterfication can be catalyzed by enzymes such as lipases, preferably *Candida antarctica* lipase B immobilized on resin (for example sold as Novozyme-435 by Novozyme, Denmark). Enzymatic transesterfication are especially beneficial in embodiments of this invention that are applied in (bio)medical or cosmetic applications that require complete absence of any residual metal catalyst.

Alternatively, both copolymerization procedures (i.e. chain extension and redistribution) may be combined to obtain polymers according to the invention.

Applications

The copolymers according to the invention are in particular suitable for applications related to personal care (hair preparations, skin cosmetics and laundry aids), surface coatings (leather, textile, optical fibers, paper and paint formulations), imaging technologies (printing, stereolithography, photography and lithography), biomedical applications (materials for controlled release of drugs and materials for tissue-engineering, tablet formulation), (thermo)reversible coatings, adhesive and sealing compositions, and thickening agents, gelling agents and binders.

EXAMPLES

The following non-limiting examples further illustrate the preferred embodiments of the invention. When not specifically mentioned, chemicals are obtained from Aldrich.

Building Blocks

Building Block 1:

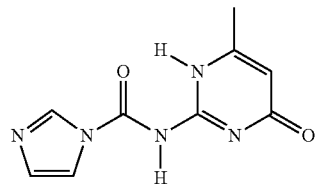

A mixture of methylisocytosine (10 g) and carbodiimidazole (CDI; 20.7 g) in dried DMSO (50 mL) was heated and stirred at 100° C. under an argon atmosphere for 2 hours. The resulting solid was filtered after cooling and washed with dry acetone until a white powder remained in the filter, that subsequently was dried in vacuo and stored over $P_2O_5$. FT-IR (neat): ν (cm$^{-1}$) 3174, 1701, 1644, 1600, 1479, 1375, 1320, 1276.

Building Block 2:

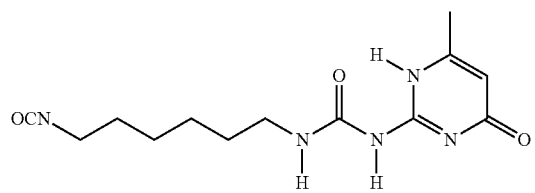

1,6-Hexyldiisocyanate (650 g) and methylisocytosine (or 2-amino-4-hydroxy-6-methyl-pyrimidine, 65.1 g) were suspended in a 2-liter flask. The mixture was stirred overnight at 100° C. under an argon atmosphere. After cooling to room temperature, a litre of pentane was added to the suspension, while stirring was continued. The product was filtered, washed with several portions of pentane and dried in vacuum. A white powder was obtained. $^1$H NMR (400 MHz, CDCl$_3$): δ 13.1 (1H), 11.8 (1H), 10.1 (1H), 5.8 (1H), 3.3 (4H), 2.1 (3H), 1.6 (4H), 1.4 (4H). FT-IR (neat): ν (cm$^{-1}$) 2935, 2281, 1698, 1668, 1582, 1524, 1256.

Building Block 3:

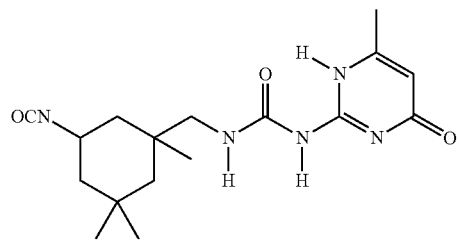

Methylisocytosine (5.2 g) was added to isophoronediisocyanate (IPDI, 50 mL) and subsequently stirred at 90° C. under an argon atmosphere for 3 days. The resulting clear solution was precipitated in heptane. The white gum was collected, heated in 150 mL heptane, cooled on ice, and filtered. The same procedure was repeated once more with the white residue, resulting in a white powder. $^1$H NMR (400 MHz, CDCl$_3$): δ 13.1 (1H), 12.0 (1H), 10.1 (1H), 5.9 (1H), 4.1-3.1 (3H), 2.1 (3H), 2.0-0.9 (15H). FT-IR (neat): ν (cm$^{-1}$) 2954, 2255, 1696, 1662, 1582, 1524, 1247. The product exists in four different isomers: two regio-isomers, one of which is shown above, exist in cis and trans configuration. For reasons of clarity, only one isomer is shown.

Synthesis of Monomer (a) Compounds
Monomer a1

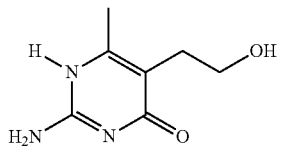

2-Acetylbutyrolactone (2 mL) and guanidine carbonate (3.3 g) were put to reflux in absolute ethanol (20 mL) in the presence of triethylamine (5.2 mL). The solution became yellow and turbid. After overnight heating at reflux, the solid was filtered, washed with ethanol, and suspended in water. The pH was adjusted to a value of 6-7 with an HCl-solution, and the mixture was stirred for a while. Filtration, rinsing of the residue with water and ethanol and subsequent drying of the solid gave the pure product. $^1$H NMR (400 MHz, DMSO-$d_6$): δ 11.2 (1H), 6.6 (2H), 4.5 (1H), 3.4 (2H), 2.5 (2H), 2.1 (3H). FT-IR (neat): ν (cm$^{-1}$) 3333, 3073, 2871, 1639, 1609, 1541, 1487, 1393, 1233, 1051, 915, 853, 789, 716.
Monomer a2:

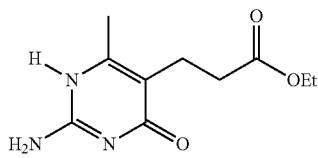

A mixture of guanidine carbonate (20 gram), diethyl-2-acetylglutarate (12 mL) and ethanol (100 mL) was put to reflux during 24 hours. The volatiles were removed by evaporation, the remaining solids were dissolved in cold water and the solution was acidified to ca. pH=6. The suspension was stirred for a few minutes and filtered. The residue was washed with some water, then with ethanol and was dried in a vaccuum stove. Yield: 61%. $^1$H NMR (400 MHz, DMSO-$d_6$): δ 6.8 (2H), 4.0 (2H), 2.5 (2H), 2.4 (2H), 2.1 (3H), 1.2 (3H).
Monomer a3:

Monomer a1 (1 g) was suspended in 1,6-hexyldiisocyanate (12 mL) and pyridine (1 mL) and was stirred at 90° C. A clear solution developed, and thereafter some gel particles formed (unwanted). The solution was cooled and filtered through some celite. The filtrate was dropped into pentane giving a white precipitate. This precipitate was again stirred in pentane to remove the last traces of 1,6-hexyldiisocyanate. Isolation via filtration was followed by drying, giving the pure diisocyanate. $^1$H NMR (400 MHz, CDCl$_3$): δ 13.1 (1H), 11.9 (1H), 10.2 (1H), 4.8-4.6 (1H), 4.2 (2H), 3.3 (6H), 3.1 (2H), 2.7 (2H), 2.3 (3H), 1.7-1.2 (16H). FT-IR (neat): ν (cm$^{-1}$) 3314, 2936, 2263, 1688, 1662, 1640, 1590, 1535, 1444, 1257, 1140, 1025, 780, 742.
Monomer a4:

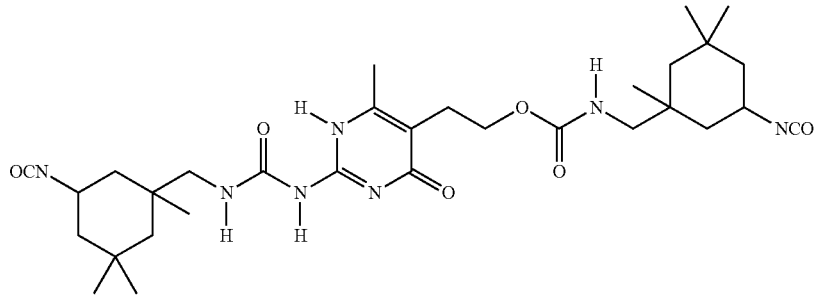

Monomer a1 (12 gram) was suspended in IPDI (150 mL) and was stirred overnight at 90° C. under an argon atmosphere. A clear solution developed. The solution was cooled and precipitated in hexane. The solid was filtered, stirred in another portion of hexane, and then the product was isolated by filtration, washing with hexane and drying of the residue. Yield: 98%. $^1$H NMR (400 MHz, CDCl$_3$): δ 13.1 (1H), 11.9 (1H), 10.2 (1H), 4.8-4.5 (1H), 4.2 (2H), 4.0-3.2 (3H), 3.1-2.9 (3H), 2.7 (2H), 2.3 (3H), 1.9-1.6 (4H), 1.4-0.8 (26H). FT-IR (neat): ν (cm$^{-1}$), 2954, 2254, 1690, 1664, 1637, 1590, 1532, 1461, 1364, 1307, 1257, 1034, 791. MALDI-TOF-MS, [M$^+$]=614, [M+Na$^+$]=636. For convenience, only one isomer of the product is shown. IPDI exists in different regio- and stereoisomers, and the coupling is not selective for one of the isocyanate functions in IPDI.
Monomer a5:

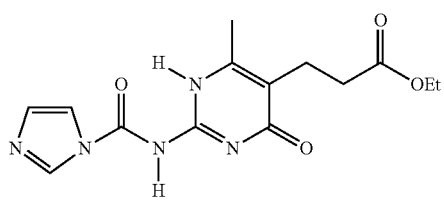

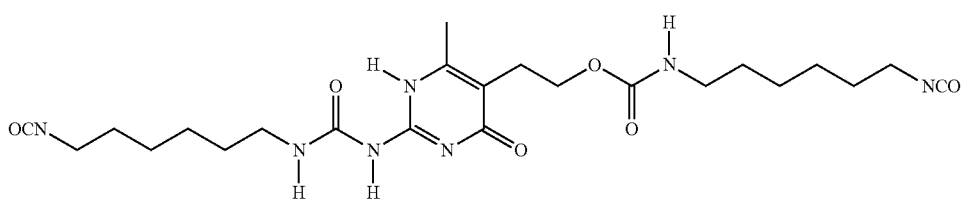

Monomer a2 (7.1 g), carbodiimidazole (8.23 g; CDI) and DMF (50 mL) were stirred under an argon atmosphere at an oil bath temperature of 100° C. The mixture became clear during the 3 hours reaction time. Cooling and addition of dry acetone induced precipitation. The residue was washed with acetone and dried. $^1$H NMR (300 MHz, DMSO-d$_6$): δ 8.3 (1H), 7.6 (1H), 7.0 (1H), 6.6 (2H), 4.0 (2H), 2.5 (2H), 2.4 (2H), 2.1 (3H), 1.2 (3H).

Monomer a6:

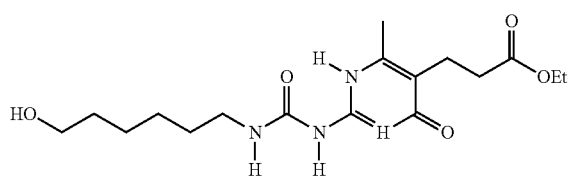

Monomer a5 and 6-amino-1-hexanol were mixed in equimolar amounts in chloroform. The mixture was refluxed and became clear during the overnight reaction that was executed under an argon atmosphere. The solution was extracted with an aqueous NaCl solution and with water, and was then dried with Na$_2$SO$_4$. Precipitation in hexane gave a white solid. $^1$H NMR (300 MHz, CDCl$_3$): δ 13.0 (1H), 11.9 (1H), 10.1 (1H), 4.9 (1H), 4.1 (2H), 3.7 (2H), 3.3 (2H), 2.7 (2H), 2.6 (2H), 2.3 (3H), 1.6 (4H), 1.4 (4H), 1.3 (3H).

Monomer a7:

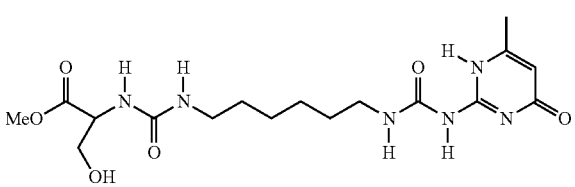

Triethylamine (1.6 mL) was added to a suspension of the HCl-salt of L-serine (1.56 gram) in dry chloroform (25 mL). The isocyanate building block 2 (2.95 g) was added and the mixture was stirred overnight at 60° C. under an argon atmosphere. The precipitate was first stirred in CHCl$_3$, filtered and washed and then this procedure was repeated in ethanol. The yield of the dried powder product was 80%. $^1$H NMR (300 MHz, DMSO-d$_6$): δ 10.6 (1H), 7.6 (1H), 6.6 (1H), 6.3 (1H), 6.2 (1H), 5.7 (1H), 5.1 (1H), 4.2 (1H), 3.8-3.3 (5H), 3.1 (2H), 3.0 (2H), 2.1 (3H), 1.5-1.2 (8H). FT-IR (neat): ν (cm$^{-1}$) 3329, 2936, 2605, 1736, 1703, 1659, 1623, 1567, 1525, 1436, 1253, 1036, 741.

Monomer a8:

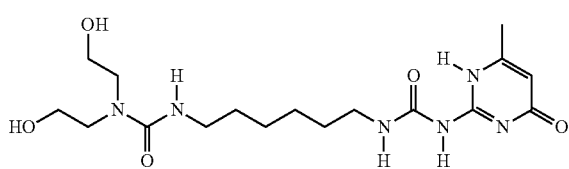

Diethanolamine (1.33 g) and the isocyanate building block 2 (3.7 g) were mixed in 30 mL THF. The suspension was put to reflux under an argon atmosphere during 20 hours. The suspension was filtered after cooling down, the residue was washed with THF and the yellow waxy compound was dried. Yield 86%. $^1$H NMR (300 MHz, DMSO-d$_6$): δ 10.7 (1H), 7.7 (1H), 6.7 (1H), 6.3 (1H), 5.7 (1H), 4.8 (2H), 3.5 (4H), 3.3 (4H), 3.2 (2H), 3.0 (2H), 2.1 (3H), 1.5-1.2 (8H). FT-IR (neat): ν (cm$^{-1}$) 3324, 3212, 2930, 1698, 1662, 1584, 1526, 1253, 1074, 765, 740.

Monomer a9:

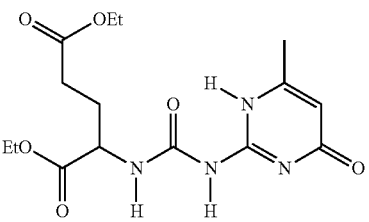

The hydrogen chloride acid of L-glutamic acid diethylester (1.02 g) was dissolved in 15 mL THF in the presence of 0.65 mL triethylamine. To this solution building block 1 was added and subsequently stirred under an argon atmosphere. After 20 hours, acetone (15 mL) was added and the mixture was subsequently filtered. The residue was washed with acetone and the white powder was dried in vacuo. Yield 82%. $^1$H NMR (300 MHz, DMSO-d$_6$): δ 7.1 (1H), 5.8 (1H), 4.4 (1H), 4.2-4.0 (4H), 3.1 (4H), 2.1 (3H), 1.2 (6H). FT-IR (neat): ν (cm$^{-1}$) 2938, 2603, 1753, 1731, 1699, 1668, 1638, 1591, 1529, 1261, 1208, 1027, 805.

Monomer a10

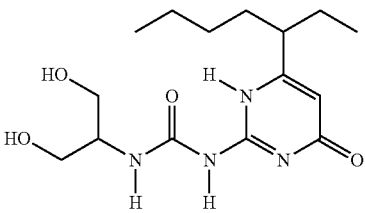

2-Amino-1,3-propanediol (0.54 g) was added to building block 1 (2.2 g) were mixed in 15 mL THF. The suspension was stirred at room temperature under an argon atmosphere during 20 hours. The solution was subsequently washed three times with water, dried on sodium sulphate. The product crystallized from a concentrated solution, and was subsequently isolated aw a white powder by filtration. Yield 63%. $^1$H NMR (300 MHz, DMSO-d$_6$): δ 10.7 (1H), 7.7 (1H), 5.7 (1H), 5.0-4.8 (1H), 3.8-3.4 (8H), 2.3 (1H), 1.8-1.1 (7H), 0.8 (6H). FT-IR (neat): ν (cm$^{-1}$) 3214, 2930, 1694, 1646, 1557, 1526, 1457, 1243, 1048, 765.

Monomer a12:

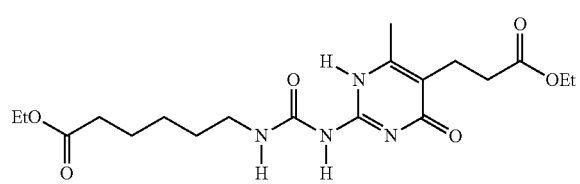

Monomer a2 (1.23 g) was dispersed in 10 mL THF, followed by the dropwise addition of ethyl 6-isocyanatohexanoate (1.2 mL). The suspension was put to reflux under an argon atmosphere during 20 hours. The suspension was filtered after cooling down, the residue was washed with THF and the white powder was isolated and dried in vacuo. Yield 92%. $^1$H NMR (400 MHz, CDCl$_3$): δ 12.9 (1H), 11.9 (1H), 10.2 (1H), 4.2 (2H), 3.3 (2H), 2.7 (2H), 2.6 (2H), 2.3 (3H), 1.7 (4H), 1.4 (2H), 1.2 (3H). FT-IR (neat): ν (cm$^{-1}$) 3214, 2982, 1729, 1698, 1661, 1642, 1584, 1264, 1188, 787.

Synthesis of Polymers (c) and (c')
Polymer c1

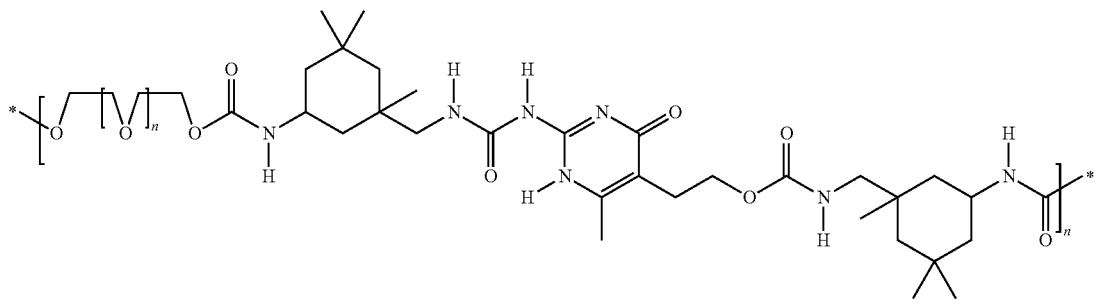

Telechelic PEO-1500 (5.83 g) was stripped three times with toluene and was then dissolved in toluene (30 mL). Monomer a4 (2.39 g) in toluene (14 mL) was added as well as a few drops of dibutyl tin dilaurate and the solution was heated overnight under argon (oil bath temperature of 120° C.). The polymer was isolated by precipitation into diethyl-ether. The material is white (semi-crystalline), elastic and tough. $^1$H NMR (300 MHz, CDCl$_3$/CD$_3$OD): δ 4.1, 3.6, 2.8, 2.2, 1.8-1.4, 1.2-0.8. SEC (THF, PS-standards): M$_w$=7.0 kD.

Polymer c2:

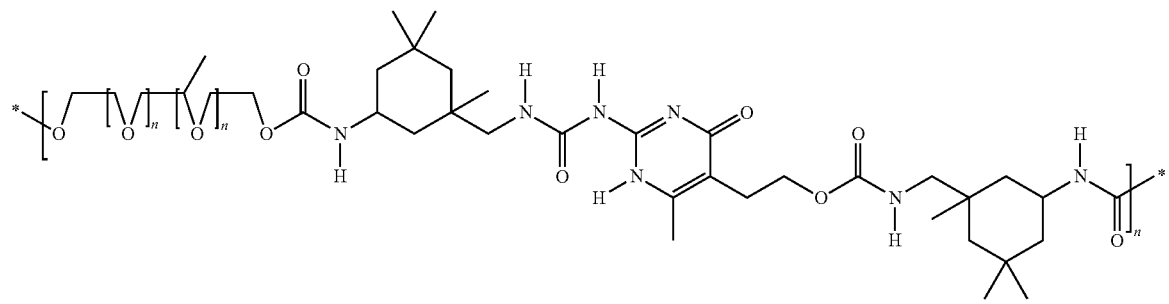

Acclaim-2220, a telechelic random co-polymer of ethylene oxide and propylene oxide with an average molecular weight of ca. 2.2 kD (3.81 g, a product of Bayer, Germany), monomer a4 (1.05 g) and a drop of dibutyl tin dilaurate were mixed in toluene (10 mL) and pyridine (1 mL) and the solution was stirred overnight under argon at an oil bath temperature of 120° C. The product was isolated by evaporation of the solvents precipitation into hexane. The material is a colourless, elastic material.

$^1$H NMR (300 MHz, CDCl$_3$/MeOH): δ 5.4-4.8, 4.4-3.2, 2.9, 2.4-2.0, 1.7, 1.5-0.6. SEC (THF, PS-standards): M$_n$=12.1 kD, D=1.6.

Polymer c3:

Kraton L2203 (11.2 g, a product of Kraton Polymers, USA), a telechelic alcohol terminated polybutylene/ethylene, in 20 mL of chloroform was added drop wise to a solution of IPDI (1.46 g) and a few drops of dibutyl tin dilaurate in chloroform (5 mL). Overnight stirring under argon was followed by heating of the solution at 40° C. for an hour. The solvent was removed by evaporation, pyridine (25 mL) and monomer a1 (0.56 g) were added and the resulting mixture was stirred overnight at an oil bath temperature of 90° C. The pyridine was evaporated and the polymer was isolated by precipitation from chloroform/ethanol 10:1 into methanol, and consecutive drying of the solid. The precipitated polymer is a white, soft and elastic material. $^1$H NMR (300 MHz, CDCl$_3$): δ 4.1, 3.8, 3.0, 2.8, 2.3, 1.5-0.8. SEC (THF, PS-standards): M$_n$=19.7 kD, D=2.1.

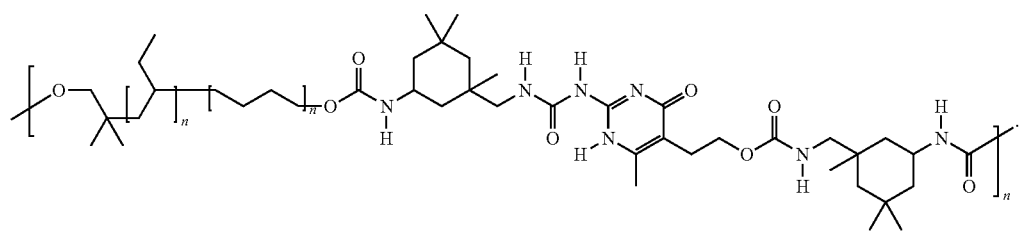

Polymer c4:

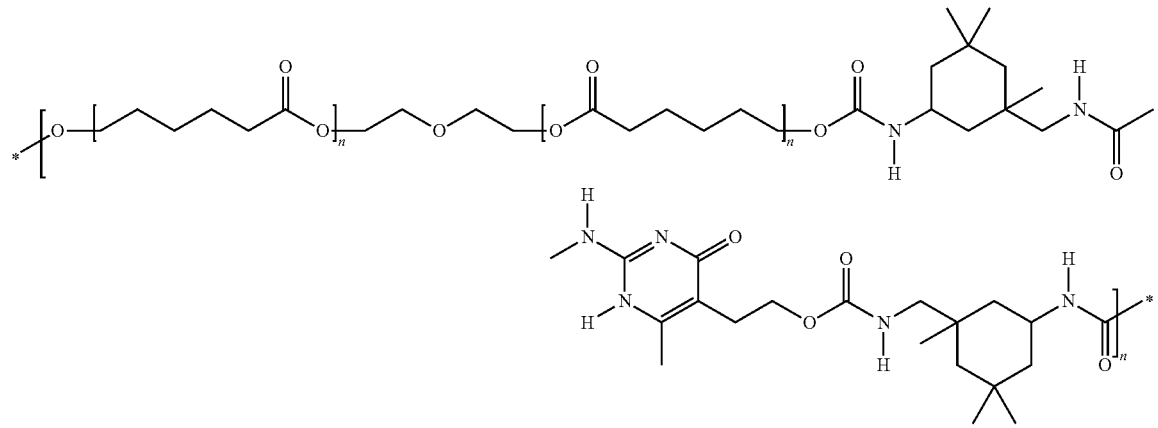

Telechelic hydroxy terminated polycaprolacton with a molecular weight of 2.0 kD (9.73 g), monomer a4 (2.5 g) and a few drops of dibutyl tin dilaurate were dissolved in chloroform (100 mL) and stirred overnight at an oil bath temperature of 60° C. The next day the chloroform was evaporated, toluene (100 mL) and pyridine (20 mL) were added, as well as a second portion of monomer a4 (0.5 g). The mixture was heated at an oil bath temperature of 120° C. for another night, and the polymer product was isolated by evaporation of the pyridine, precipitation from chloroform/methanol 10:1 into methanol and drying of the solid. Upon standing the material develops into a white (semi-crystalline), elastic polymer. $^1$H NMR (300 MHz, CDCl$_3$): δ 12.0, 10.1, 4.5-3.8, 3.0, 2.6-2.2, 2.0-0.8. SEC (THF, PS-standards): M$_n$=38.5 kD, D=2.0.
Polymers c5:

pate) with monomer a4 in different molar ratios. In all cases an excess of polyester has been used and this excess determines the average molecular weight and the average number of quadruple hydrogen bonds in the backbone of the polymer product. Optionally, the hydroxy groups remaining in the polymer product can be capped with building block 3.

Typical procedure (polymer c5-c): Telechelic poly(2-methyl-1,3-propylene adipate) (average molecular weight Mn=2.0 kD, hydroxy end groups, 5.0 g) was stripped three times with toluene and dissolved in chloroform (25 mL) together with monomer a4 (1.16 g) and few drops dibutyl tin dilaurate. The mixture was boiled overnight. The next day, the absence of isocyanate functions was checked using FT-IR spectroscopy, the required amount of building block 3 (0.46 g) was added and the solution was put to reflux for another

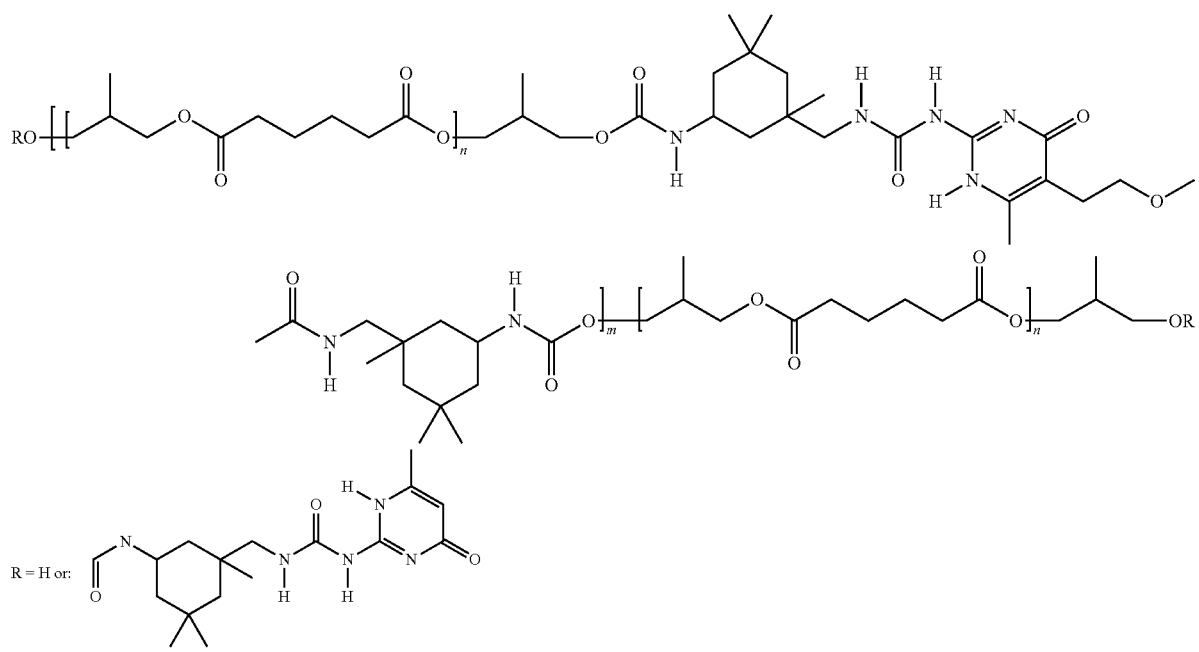

A range of chain extended poly(2-methyl-1,3-propylene adipate) polymers have been prepared by reacting a hydroxy functionalized telechelic poly(2-methyl-1,3-propylene adipate) with monomer a4 in different molar ratios. In all cases night. Again, it was verified with FT-IR whether the isocyanate-functions had disappeared, and the polymer was isolated by precipitation from a chloroform/methanol solution into ether and drying of the solid. If the reaction mixture became too viscous, dry chloroform or THF solvent was added. Typical NMR (polymer c10-a): $^1$H NMR (300 MHz, CDCl$_3$): δ 12.0-11.8, 10.1-9.8, 5.8, 5.0-4.6, 4.3-3.8, 3.4-2.8, 2.5-2.0, 1.9-1.6, 1.4-0.8.

The following table lists the prepared poly(2-methyl-1,3-propylene adipate) polymers, polymers c5-a-c5-d have been capped with building block 3, while polymers c5-e-c5-h have not been capped (i.e. R=H).

| Polymer | Amount of telechelic polyester (g; mmol) | Amount of a4 (g; mmol) | Building block 3 (g; mmol) | Theoretical 4H-units per polymer chain (average) | Theoretical mol. weight Mn (kg/mol) | Measured $M_n$ and D (SEC)* |
|---|---|---|---|---|---|---|
| c5-a | 9.27; 4.64 | 1.42; 2.31 | 1.61; 4.64 | ca. 3 | 5.3 | 5.3; 1.8 |
| c5-b | 4.95; 2.48 | 1.01; 1.65 | 0.60; 1.73 | ca. 4 | 7.9 | 7.2; 2.0 |
| c5-c | 5.02; 2.51 | 1.16; 1.89 | 0.46; 1.32 | ca. 5 | 10.5 | 10.2; 1.9 |
| c5-d | 5.48; 2.74 | 1.35; 2.19 | 0.40; 1.15 | ca. 6 | 13.1 | 9.3; 2.3 |
| c5-e | 5.55; 2.78 | 1.13; 1.84 | — | ca. 2 | 7.2 | 5.6; 2.6 |
| c5-f | 5.32; 2.66 | 1.31; 2.14 | — | ca. 4 | 12.5 | 15.5; 1.7 |
| c5-g | 10.05; 5.03 | 3.08; 5.02 | — | infinite | infinite | 74; 2.1 |

*Using THF as eluent, UV-detection and applying polystyrene standards

Polymer c6: Chain Extended Poly(caprolactone)

Telechelic hydroxy terminated polycaprolacton with a molecular weight of 2.0 kD (9.22 g), was stripped three times with toluene and dissolved in chloroform (50 mL) together with monomer a4 (2.26 g) and few drops dibutyl tin dilaurate. The mixture stirred overnight at 60° C., followed by confirming the absence of isocyanate functions with FT-IR spectroscopy. Building block 3 (0.67 g) was added and the solution diluted with 25 mL chloroform and put to reflux for another night. Again, it was verified with FT-IR whether the isocyanate-functions had disappeared, and the polymer was isolated by precipitation from a chloroform/ethanol solution into hexane and drying of the solid. $^1$H NMR (300 MHz, CDCl$_3$): δ 12.0, 10.1, 4.5-3.8, 3.0-2.8, 2.6-2.2, 2.0-0.8. SEC (THF, PS-standards): $M_n$=11.5 kD, D=2.0.

Polymer c7: Copolymer with Poly(2-methyl-1,3-propylene Adipate) and Polycaprolactone-Blocks A mixture of telechelic hydroxy terminated poly(2-methyl-1,3-propylene adipate) with an average molecular weight of 2.0 kD (2.39 g) and telechelic hydroxy terminated polycaprolactone with an average molecular weight of 2.0 kD (2.39 g), was stripped three times with toluene and dissolved in chloroform (25 mL) together with monomer a4 (1.18 g) and few drops dibutyl tin dilaurate. The mixture stirred overnight at 60° C., followed by confirming the absence of isocyanate functions with FT-IR spectroscopy, building block 3 (0.35 g) was added and the solution diluted with 20 mL chloroform and put to reflux for another night. Again, it was verified with FT-IR whether the isocyanate-functions had disappeared, and the polymer was isolated by precipitation from a chloroform/ethanol solution into hexane and drying of the solid. $^1$H NMR (300 MHz, CDCl$_3$): δ 13.2-12.8, 12.1-11.8, 10.2-9.8, 5.8, 5.2-4.5, 4.4-3.6, 3.4-2.6, 2.6-2.0, 2.0-0.6. SEC (THF, PS-standards): $M_n$=12.2 kD, D=

Polymer c8: Mixture of Chain Extended Polycaprolactone and poly(2-methyl-1,3-propylene adipate)

Polymer c6 (2.2 g) and polymer c5-c (2.2 g) were dissolved in a hot mixture of 20 mL chloroform and 5 mL ethanol. The resulting viscous solution was poured into a mold and subsequently dried at atmospheric pressure, giving an elastic transparent film.

Polymer c9: Polycaprolactone Resditributed with 4H-Unit

Polycaprolactone with a molecular weight of 10 kD (0.35 g), was stripped three times with toluene. To this polymer was added monomer a6 (76 mg) and toluene (10 mL) in a Schlenck-flask in a nitrogen atmosphere. Subsequently, Novozym 435 (37 mg, immobilized *C. antarctica* lipase B a product from Novo Nordisk, Denmark) was added and the mixture was heated to 90° C. After stirring for 18 hours, the reaction mixture was diluted with chloroform (10 mL), filtered, concentrated and precipitated in methanol, resulting in a white fiber like material after drying of the solid. $^1$H NMR (400 MHz, CDCl$_3$): δ 12.9, 11.9, 10.2, 4.3-3.8, 3.7, 3.3, 2.7, 2.6, 2.4-2.2, 1.9-1.2. SEC (THF, PS-standards): $M_n$=13.5 kD, D=1.5.

Enhanced Material Properties of Chain-Extended Polyesters.

The following table shows the enhancement in material properties obtained for different polymers after chain extension with the 4H-unit. The resulting polymers c5-d, c6, c7, and c8, all show pronounced elastic behavior, whereas the non-chain extended polyesters display no elastic behavior, i.e. the starting poly(2-methyl-1,3-propylene adipate) is a liquid, and the starting polycaprolactone is a brittle crystalline material.

| Polymer | $T_g$ (° C.) | $T_m$ (° C.)$^a$ | $E_{mod}^{a,b}$ |
|---|---|---|---|
| c5-d | −38 | — | 1.6 |
| c6 | −46 | 49 | 19.3 |
| c7 | −43 | — | 1.7 |
| c8 | −46 | — | 2.9 |

$^a$measured on pristine samples
$^b$Elastic modulus $E_{mod}$ is measured according to DIN 53 457/1987

The invention claimed is:

1. A process for the preparation of a supramolecular polymer comprising quadruple hydrogen bonding units within the polymer backbone, wherein at least a monomer comprising a 4H unit is incorporated in the polymer backbone via two to four reactive groups, and the 4H units are incorporated in the polymer backbone by two covalent bonds, the process comprising reacting in a bulk polymerization a monomeric unit (a) having a structure according to the following formulae:

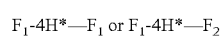

with a macromonomeric unit (b) having a structure according to formula (V):

(V)

wherein
s is 2-6, and
P represents a polymer chain having a number average molecular weight of 100 to 100,000; and
wherein the 4H* unit is represented by formula (VIIa) and (VIIb), and tautomers and/or enantiomers thereof:

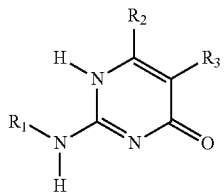

(VIIa)

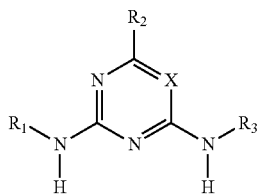

(VIIb)

wherein the 4H* unit is connected to $F_1$ via $R_1$ and to $F_1$ or $F_2$ via $R_3$, wherein $R_2$ is a random side chain or a hydrogen atom, the random side chain being a linear, cyclic or branched alkyl group comprising 1 to 7 carbon atoms, X is a nitrogen atom or a carbon atom to which a group $R_4$ is attached, $R_1$-$R_4$ are selected from the group consisting of hydrogen atoms and shorter or longer chains, the longer and shorter chains being selected from the group consisting of saturated or unsaturated, branched, cyclic or linear alkyl chains, aryl chains, alkaryl chains, arylalkyl chains, ester chains and ether chains.

2. The process according to claim 1, wherein the monomeric unit (a) comprises a 4H* unit represented by formula (VIIa).

3. The process according to claim 1, wherein the process proceeds by chain extension.

4. The process according to claim 1, wherein monomeric unit (a) is represented by $F_1$-4H*—$F_1$ and the macromonomeric unit (b) is represented by $F_3$—P—$F_3$, wherein $F_1$ and $F_3$ are complementary reactive groups.

5. The process according to claim 1, wherein monomeric unit (a) is represented by $F_1$-4H*—$F_2$ and the macromonomeric unit (b) is represented by $F_3$—P—$F_3$, wherein $F_1$ and $F_3$ are complementary reactive groups and $F_2$ and $F_3$ are complementary reactive groups.

6. The process according to claim 5, wherein $F_1$, $F_2$ and $F_3$ are independently selected from the group consisting of —$NH_2$, —NHR, —NCO, blocked —NCO, —OH, —C(O)OH, and —C(O)OR, wherein R is a linear or branched $C_1$-$C_6$ alkyl group, a $C_6$-$C_{12}$ arylgroup, a $C_7$-$C_{12}$ alkaryl group or a $C_7$-$C_{12}$ alkylaryl group, or a halogen atom selected from the group consisting of Cl, Br and I.

7. The process according to claim 5, wherein monomeric unit (a) has the formula $F_1$-4H*—$F_2$, wherein $F_1$ is amino and $F_2$ is hydroxy, and wherein macromonomeric unit (b) has the formula $F_3$—P—$F_3$, wherein $F_3$ is isocyanate.

8. The process according to claim 1, wherein two or more macromonomeric units (b) having a different number average molecular weight are used.

9. The process according to claim 1, wherein two or more macromonomeric units (b) having a different molecular structure are used.

10. The process according to claim 1, wherein a stopper-molecule is used.

11. The process according to claim 10, wherein the stopper molecule has the formula P—$F_1$, 4H—$F_1$ or 4H*—$F_1$, wherein $F_1$, 4H and 4H* are as defined in the preceding claims.

12. The process according to claim 1, wherein a branching species is used.

13. The process according to claim 12, wherein the branching species has the formula P—$(F_i)_u$ or 4H*—$(F_i)_u$, wherein u is 3-6.

14. The process according to claim 1, wherein the molar ratio between monomeric unit (a) and macromonomeric unit (b) is between 1:2 and 2:1.

15. The process according to claim 1, wherein monomeric unit (a) has one of the following structures:

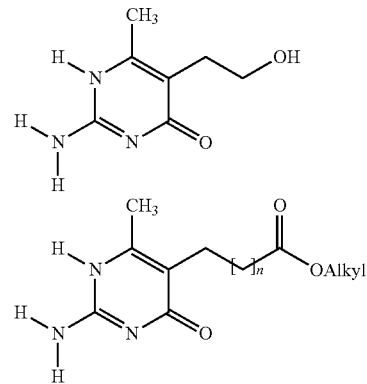

wherein n is 1 or 2, and alkyl is methyl or ethyl.

16. The process according to claim 1, wherein the macromonomeric unit (b) is obtained by reacting a polymer with about two hydroxyl end groups with about two equivalents of a diisocyanate.

17. The process according to claim 16, wherein the diisocyanate is selected from the group consisting of toluene diisocyanate, methylene diphenyl diisocyanate, methylene dicyclohexane 4,4-diisocyanate, isophorone diisocyanate, hexane diisocyanate, 1,6-diisocyanato-2,2,4-trimethylhexane and 1,6-diisocyanato-2,4,4-trimethylhexane.

* * * * *